(12) United States Patent
Nishino et al.

(10) Patent No.: US 9,753,158 B2
(45) Date of Patent: Sep. 5, 2017

(54) RADIOGRAPHIC IMAGING APPARATUS, RADIOGRAPHIC IMAGING SYSTEM, AND RADIOGRAPHIC IMAGING METHOD

(71) Applicant: FUJIFILM Corporation, Tokyo (JP)

(72) Inventors: Naoyuki Nishino, Kanagawa (JP); Naoto Iwakiri, Kanagawa (JP); Takeyasu Kobayashi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 301 days.

(21) Appl. No.: 14/259,669

(22) Filed: Apr. 23, 2014

(65) Prior Publication Data

US 2014/0219422 A1 Aug. 7, 2014

Related U.S. Application Data

(63) Continuation-in-part of application No. PCT/JP2012/077268, filed on Oct. 22, 2012.

(30) Foreign Application Priority Data

Nov. 1, 2011 (JP) ................................. 2011-240514
Nov. 1, 2011 (JP) ................................. 2011-240515

(51) Int. Cl.
*G01T 1/24* (2006.01)
*A61B 6/03* (2006.01)
(Continued)

(52) U.S. Cl.
CPC ............ *G01T 1/247* (2013.01); *A61B 6/5258* (2013.01); *A61B 6/582* (2013.01); *G01T 1/246* (2013.01);
(Continued)

(58) Field of Classification Search
CPC .. A61B 6/00; A61B 6/032; A61B 6/42; A61B 6/4208; A61B 6/4233;
(Continued)

(56) References Cited

U.S. PATENT DOCUMENTS 5,046,147 A * 9/1991 Funahashi ............... G06T 5/009
250/587
6,163,029 A * 12/2000 Yamada ................... G01T 1/247
250/370.01
(Continued)

OTHER PUBLICATIONS

International Search Report issued in PCT/JP2012/077268 dated Nov. 20, 2012.
Written Opinion issued in PCT/JP2012/077268 dated Nov. 20, 2012.

*Primary Examiner* — Anastasia Midkiff
(74) *Attorney, Agent, or Firm* — Edwards Neils LLC; Jean C. Edwards, Esq.

(57) ABSTRACT

There are provided the following components: an FPD that has a plurality of pixels, in which signal electric charges corresponding to amounts of X-rays incident are accumulated, and that is capable of nondestructively reading data which indicates the X-ray image; an amplifier that amplifies a signal sent from the FPD and has a variable gain; an evaluation value calculation section that obtains an evaluation value for evaluating the X-ray image; and a gain adjustment section that calculates a new gain of the amplifier used at the time of rereading. The gain of the amplifier is changed to a value of a new gain which is calculated by the gain adjustment section, and the X-ray image is reread.

30 Claims, 18 Drawing Sheets

(51) Int. Cl.

| | | |
|---|---|---|
| *G06T 11/00* | (2006.01) | |
| *G06K 9/62* | (2006.01) | |
| *H04N 5/32* | (2006.01) | |
| *A61B 6/00* | (2006.01) | |
| *H04N 5/347* | (2011.01) | |
| *H04N 5/359* | (2011.01) | |
| *H04N 5/363* | (2011.01) | |
| *G06T 5/00* | (2006.01) | |
| *H04N 5/378* | (2011.01) | |
| *H04N 5/369* | (2011.01) | |
| *G03B 42/04* | (2006.01) | |
| *H04N 5/235* | (2006.01) | |
| *H04N 5/243* | (2006.01) | |

(52) U.S. Cl.
CPC .......... *G06K 9/6202* (2013.01); *G06T 11/005* (2013.01); *H04N 5/32* (2013.01); *H04N 5/347* (2013.01); *H04N 5/359* (2013.01); *H04N 5/363* (2013.01); *A61B 6/4233* (2013.01); *A61B 6/4283* (2013.01); *G03B 42/04* (2013.01); *G06K 9/6201* (2013.01); *G06T 5/002* (2013.01); *H04N 5/2351* (2013.01); *H04N 5/243* (2013.01); *H04N 5/369* (2013.01); *H04N 5/378* (2013.01)

(58) Field of Classification Search
CPC ....... A61B 6/4283; A61B 6/52; A61B 6/5211; A61B 6/5229; A61B 6/5235; A61B 6/5258; A61B 6/58; A61B 6/582; G06T 1/00; G06T 1/60; G06T 5/00; G06T 5/001; G06T 5/002; G06T 5/40; G06T 5/50; G06T 11/00; G06T 11/003; G06T 11/005; G06T 2207/00; G06T 2207/10072; G06T 2207/10081; G06T 2207/10116; G06T 2207/20; G06T 2207/20004; G06T 2207/20012; G06T 2207/20072; G06T 2207/20182; G06T 2207/204; G06T 2207/212; G06T 2207/221; G06T 2210/00; G06T 2210/41; G06T 2211/00; G06T 2211/40; G06T 2211/412; G06T 2211/424; G01T 1/00; G01T 1/16; G01T 1/20; G01T 1/2006; G01T 1/2017; G01T 1/24; G01T 1/244–1/247; G01T 7/00; G01T 7/005; G06K 9/36; G06K 9/38; G06K 9/40; G06K 9/46; G06K 9/4642; G06K 9/4647; G06K 9/52; G06K 9/60; G06K 9/62; G06K 9/6201; G06K 9/6202; G06K 9/6212; G06K 9/6288; G06K 9/6289; G06K 9/629; G06K 9/6298; G06K 9/68; G06K 9/78; G06K 9/80; G06K 2009/6213; H04N 1/38; H04N 1/387; H04N 1/3871; H04N 1/3876; H04N 1/40; H04N 1/401; H04N 1/407; H04N 1/4072; H04N 1/4074; H04N 1/409; H04N 2201/0096; H04N 2201/04; H04N 2201/0402; H04N 2201/0414; H04N 5/00; H04N 5/21; H04N 5/217; H04N 5/225; H04N 5/2251–5/2253; H04N 5/2258; H04N 5/23229; H04N 5/232354; H04N 5/235; H04N 5/2351; H04N 5/2355; H04N 5/243; H04N 5/30; H04N 5/32; H04N 5/334; H04N 5/341; H04N 5/345; H04N 5/3456; H04N 5/347; H04N 5/351; H04N 5/355; H04N 5/35536; H04N 5/35545; H04N 5/357; H04N 5/359; H04N 5/363; H04N 5/365; H04N 5/369; H04N 5/374; H04N 5/3745; H04N 5/37457; H04N 5/378; H04N 5/44; H04N 5/42; H04N 5/52

See application file for complete search history.

(56) References Cited

U.S. PATENT DOCUMENTS

| | | | | |
|---|---|---|---|---|
| 2002/0049376 | A1* | 4/2002 | Takeo | A61B 10/0041 600/407 |
| 2007/0187609 | A1* | 8/2007 | Karim | H04N 3/155 250/370.09 |
| 2009/0161979 | A1* | 6/2009 | Kim | H04N 1/407 382/261 |
| 2012/0132820 | A1* | 5/2012 | Iwakiri | G01T 1/2018 250/370.08 |
| 2012/0132824 | A1* | 5/2012 | Nishino | H04N 5/32 250/394 |
| 2013/0136234 | A1* | 5/2013 | Noma | H05G 1/64 378/91 |
| 2013/0140465 | A1* | 6/2013 | Nishinou | G01T 1/24 250/366 |

\* cited by examiner

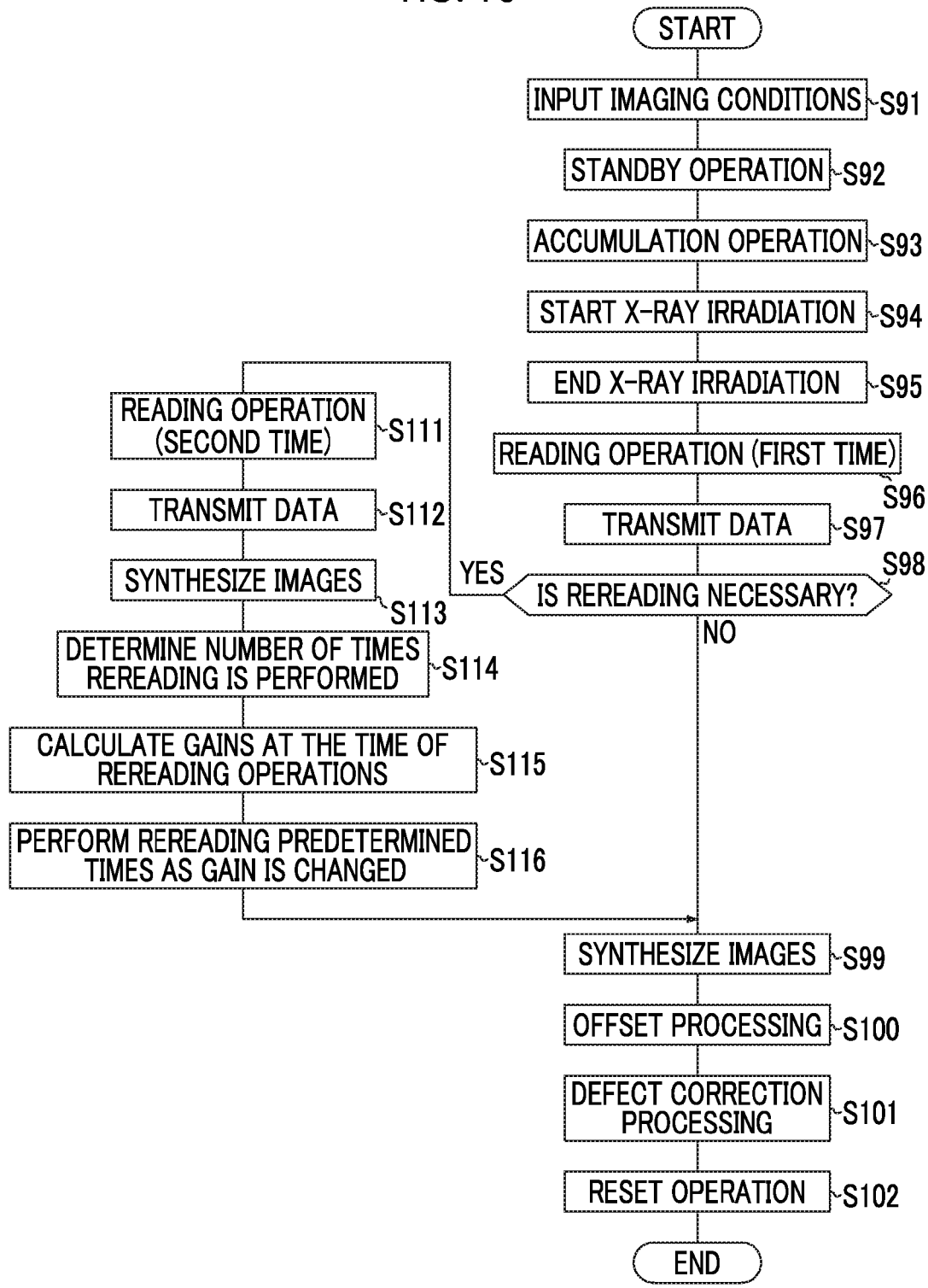

RADIOGRAPHIC IMAGING APPARATUS, RADIOGRAPHIC IMAGING SYSTEM, AND RADIOGRAPHIC IMAGING METHOD

CROSS-REFERENCE TO RELATED APPLICATIONS

This application is a Continuation of PCT International Application No. PCT/JP2012/077268 filed on Oct. 22, 2012, which was published under PCT Article Japanese, and which in turn claims priority under 35 U.S.C §119(a) to Patent Application No. 2011-240514 filed in Japan on Nov. 1, 2011 and Patent Application No. 2011-240515 filed in Japan on Nov. 1, 2011, the contents of all of which are hereby expressly incorporated by reference into the present application.

BACKGROUND OF THE INVENTION

1. Field of the Invention

The present invention relates to a radiographic imaging apparatus, a radiographic imaging system, and a radiographic imaging method for radiographing a radiographic image of a subject by using a radiographic image detector.

2. Description of the Related Art

Recently, in the field of radiography, for example, X-ray imaging, instead of an X-ray film or an imaging plate (IP), X-ray image detection devices (hereinafter referred to as electronic cassettes) using a flat panel detector (hereinafter referred to as an FPD), which uses semiconductor elements, as a detector have been widely used. The FPD uses an image sensor formed of a so-called solid-state imaging apparatus which is formed by using the semiconductor elements, and thus the pixels, in which the signal electric charges corresponding to the amounts of incident X-rays are accumulated, are arranged in a matrix. The FPD detects an X-ray image, which indicates image information of a subject, by converting the signal electric charge, which is accumulated for each pixel due to the incidence of the X-rays, into a voltage signal. The X-ray image, which is detected by the FPD, is output as digital image data.

The FPD includes a TFT type, in which pixels including thin film transistors (TFTs) are formed on a glass substrate, and in addition a CMOS type in which pixels are formed on a silicon substrate through a process of manufacturing Complementary Metal-Oxide Semiconductor (CMOS) as described in JP2005-143802A. One of the big differences between the TFT type and the CMOS type is a way of reading the voltage signals. The TFT type FPD is a system in which the signal electric charges accumulated in the pixels are transferred to an integrating amplifier through signal lines and in which the voltage signals corresponding to the signal electric charges integrated by the integrating amplifier are read. The TFT type FPD is a so-called destructive reading system in which the signal electric charges in the pixels are drained through reading. In contrast, the CMOS type FPD is a so-called nondestructive reading system in which the amplifier converting the signal electric charge into the voltage signal is provided in each pixel and the voltage signals corresponding to the signal electric charges are read in a state where the signal electric charges are retained in the pixels.

In the FPD of either of the TFT type or the CMOS type, apparently, there is an upper limit in the amount of accumulated signal electric charge accumulated in the pixel. Thus, if there is an excessively large dosing amount of X-rays incident into the pixel, the pixel is saturated, and so-called overflow occurs. In this case, in the X-ray image, the pixel becomes a distorted black pixel. On the other hand, if there is an excessively small dosing amount of X-rays, that is, if so-called underflow occurs, in the X-ray image, the pixel becomes a distorted white pixel. In X-ray imaging, imaging conditions, such as irradiation time and tube current, determining the dosing amount of rays emitted by the X-ray source are set in advance in accordance with a physical size or an imaging target portion of a subject so as not to cause overflow and underflow.

Further, even when the amount of accumulated signal electric charge accumulated in the pixel does not cause overflow and underflow, if the gain (amplification ratio) of the amplifier at the time of reading the X-ray image is excessively high, this causes overflow, whereas if the gain (amplification ratio) of the amplifier is excessively low, this causes underflow. Hence, in order to obtain an X-ray image with better image quality, by measuring the dosing amount of rays incident into the FPD, the gain (amplification ratio) of the amplifier at the time of reading the X-ray image may be adjusted in accordance with the measured dosing amount. For example, in the CMOS type FPD of JP2005-143802A, using an advantage of a CMOS-type nondestructive reading technique, before reading the X-ray image, based on the voltage signals (pixel values) which are nondestructively read from some pixels in the detection surface, the gains (amplification ratios) of the amplifiers at the time of reading the X-ray image are adjusted.

Specifically, a plurality of determination pixels, which are distributed to be regularly spaced in the detection surface, is provided, and voltage signals (pixel values) are nondestructively read from the plurality of determination pixels during irradiation of X-rays. In addition, among the plurality of determination pixels, a determination pixel of which the pixel value is the maximum is specified as a reference pixel, and the following adjustment is performed: if the pixel value of the reference pixel is large, the gain is decreased; and if the pixel value is small, the gain is increased. As described above, when the gain is adjusted, occurrence of overflow and underflow is reduced.

SUMMARY OF THE INVENTION

However, a problem arises in that, to further reduce overflow and underflow, the method described in JP2005-143802A is not sufficient. For example, in the method of JP2005-143802A, the reference pixel finally used for gain adjustment is set as the determination pixel of which the pixel value is the maximum. However, the reference pixel tends to become a determination pixel which is positioned in a bypass region where there is no absorption of X-rays by the subject or there is no subject. A pixel value in the bypass region is greater than a pixel value in the subject region in which a subject is present, and thus the gain is adjusted to a small value. However, if the gain is adjusted based on the reference pixel in the bypass region, underflow tends to occur in the subject region which is an observation target in the X-ray image.

Further, it can be considered that all the plurality of determination pixels may be positioned in a region such as a bone portion of a subject where the X-ray transmittance is low. In this case, the gain is adjusted to a high value, but the gain becomes excessively high in a soft tissue such as a lung where the X-ray transmittance is high compared with the bone portion, and thus overflow occurs.

In terms of reducing the amount of radiation exposure of a subject in addition to improvement in image quality, it becomes more important to further appropriately perform the gain adjustment in accordance with a physical size of a subject or an imaging target portion. Accordingly, a large dosing amount is generally advantageous in obtaining an X-ray image with good image quality, but in terms of reducing the amount of radiation exposure of a subject, it is desirable that the dosing amount be made as small as possible. Then, it is inferred that the dosing amount of the X-ray source tends to be set to be as small as possible. Compared with the case where the dosing amount is large, in a case where the dosing amount is small, it is difficult to obtain an X-ray image with good image quality unless the gain adjustment is appropriately performed. Hence, in order to obtain good image quality with a small dosing amount, it becomes more important to perform appropriate gain adjustment.

Further, if radiography ends in failure due to overflow or underflow, re-radiography is necessary. However, it is apparent that this re-radiography increases the amount of radiation exposure. In terms of reliably preventing re-radiography, it is also highly necessary to appropriately perform the gain adjustment.

Furthermore, according to research of the present applicants, in a practical X-ray source, even when the dosing amount is set in the imaging conditions, there is an error between the set dosing amount and the dosing amount of rays actually emitted, and the error changes in accordance with equipment types and individual differences, but sometimes the error may be as large as 10% or more. When such an error occurs in a direction in which the dosing amount increases, the tendency to set a low dosing amount in order to reduce the amount of radiation exposure becomes stronger, and thus it becomes more necessary to appropriately perform the gain adjustment.

The present invention has been made in view of the above-mentioned problems, and its object is to reliably obtain a radiographic image with good image quality, without overflow or underflow, even when the dosing amount is small, in the radiography.

According to the present invention, there is provided a radiographic imaging apparatus including: a radiographic image detection section that receives radiation, which is emitted from a radiation source and transmitted through a subject, and detects a radiographic image of the subject, the radiographic image detection section having a plurality of pixels, in which signal electric charges corresponding to amounts of the radiation incident are accumulated, and being capable of nondestructively reading data, which indicates the radiographic image based on the amounts of the accumulated signal electric charges, from the pixels; an amplification section capable of amplifying signals corresponding to the signal electric charges and capable of varying gain used for reading the radiographic image when the radiographic image is read from the radiographic image detection section; a determination section that obtains an evaluation value for evaluating the radiographic image based on pixel values in a predetermined region of the read radiographic image, and determines whether or not performing a rereading of the radiographic image is necessary based on the evaluation value; and a gain calculation section that calculates a new gain of the amplification section used at the time of the rereading based on the evaluation value when the rereading is determined to be necessary from a result of the determination performed by the determination section, in which the gain of the amplification section is changed to a value of the new gain which is calculated by the gain calculation section, and the radiographic image is reread using the changed gain.

It is desirable that the determination section determines whether or not performing the rereading is necessary, based on an appearance frequency distribution of pixel values in the radiographic image.

It is desirable that the determination section determines whether or not performing the rereading is necessary, based on an effective range that indicates a distribution of pixel values of pixels indicating the subject depending on the appearance frequency distribution.

It is desirable that the determination section extracts pixels belonging to the effective range, set an average value of pixel values of the extracted pixels as the evaluation value, and determine whether or not the rereading is necessary, by determining that the rereading is not necessary when the evaluation value is in the predetermined range and determining that the rereading is necessary when the evaluation value is outside of the predetermined range.

It is desirable that the determination section sets an average value between a maximum value and a minimum value of the effective range as the evaluation value, and determines whether or not performing the rereading is necessary.

It is desirable that the determination section sets an amount of deviation between a width of the effective range and a predetermined width as the evaluation value, and determines whether or not performing the rereading is necessary.

It is desirable that there be provided an image synthesizing section that generates a single synthesized radiographic image by using a plurality of the radiographic images which are obtained by changing and reading the gain of the amplification section through the first reading and the rereading.

It is desirable that the image synthesizing section generates the synthesized radiographic image by replacing a pixel, of which a pixel value is saturated, in the radiographic image which is read with a high gain, with a pixel corresponding to the read radiographic image which is read with a subsequent high gain, preferentially using pixels of the radiographic image which is read with the high gain.

It is desirable that an initial value of the gain of the amplification section be determined by imaging conditions that define a dosing amount of rays emitted by a radiation source.

It is desirable that the gain of the amplification section calculated by the gain calculation section be less than that at the time of the previous reading of the radiographic image.

It is desirable that the gain of the amplification section calculated by the gain calculation section be a value equal to $(1/2)^n$ times the initial value where n is an integer other than 0.

According to the present invention, there is provided a radiographic imaging system including: a radiation source; and the radiographic imaging apparatus that receives radiation, which is emitted from the radiation source and transmitted through a subject, and radiographs a radiographic image of the subject.

According to the present invention, there is provided a radiographic imaging method including: a signal electric charge accumulation step of accumulating signal electric charges corresponding to amounts of radiation, which is emitted onto a subject and is incident into a plurality of pixels, through a radiographic image detection section having the plurality of pixels, which receives the radiation and detects a radiographic image, and being capable of nondestructively reading data, which indicates the radiographic image, from the pixels; a radiographic image reading step of reading the radiographic image by amplifying signals corresponding to the signal electric charges through an amplification section which is capable of amplifying the signals and is capable of varying gain used for reading the radiographic image when the radiographic image is read from the radiographic image detection section; a rereading necessity determination step of obtaining an evaluation value for evaluating the radiographic image based on pixel values in a predetermined region of the radiographic image, and determining whether or not performing a rereading of the radiographic image based on the evaluation value; a gain calculation step of calculating a new gain of the amplification section used at the time of the rereading based on the evaluation value when the rereading is determined to be necessary from a result of the determination as to whether or not performing the rereading is necessary; and a rereading step of changing the gain of the amplification section to the calculated gain and rereading the radiographic image using the changed gain.

Further, according to the present invention, there is provided a radiographic imaging apparatus including: a radiographic image detection section that receives radiation, which is emitted from a radiation source and transmitted through a subject, and detects a radiographic image of the subject, the radiographic image detection section having a plurality of pixels, in which signal electric charges corresponding to amounts of the radiation incident are accumulated, and being capable of nondestructively reading data, which indicates the radiographic image based on the amounts of the accumulated signal electric charges, from the pixels; an amplification section capable of amplifying signals corresponding to the signal electric charges and capable of varying gain used for reading the radiographic image when the radiographic image is read from the radiographic image detection section; an image synthesizing section that outputs the radiographic image, which is read first by the radiographic image detection section, as a synthesized radiographic image when the radiographic image is read first, and synthesizes a plurality of the radiographic images, which are read from the radiographic image detection section through the rereading, so as to generate a synthesized radiographic image when the plurality of the radiographic images is read; a determination section that obtains an evaluation value for evaluating the radiographic image based on pixel values in a whole region of the synthesized radiographic image, and determines whether or not performing a rereading of the radiographic image is necessary based on the evaluation value; and a gain calculation section that calculates a new gain of the amplification section used at the time of the rereading based on the evaluation value when the rereading is determined to be necessary from a result of the determination performed by the determination section, in which the gain of the amplification section is changed to a value of the new gain which is calculated by the gain calculation section, the radiographic image is reread using the changed gain, and a new synthesized radiographic image including the new radiographic image, which is obtained through the rereading, is generated.

It is desirable that the image synthesizing section generates the new synthesized radiographic image including the new radiographic image when the new radiographic image is obtained through the rereading.

It is desirable that the image synthesizing section generates the synthesized radiographic image by averaging the plurality of the radiographic images.

It is desirable that the image synthesizing section generates the synthesized radiographic image by replacing a pixel, of which a pixel value is saturated, in the radiographic image which is read with a high gain, with a pixel corresponding to the read radiographic image which is read with a subsequent high gain, preferentially using pixels of the radiographic image which is read with the high gain.

It is desirable that the gain calculation section calculates a gain used at the time of subsequent rereading whenever the new synthesized radiographic image is generated through the rereading.

It is desirable that an initial value of the gain of the amplification section be set in advance, and be determined by imaging conditions that define a dosing amount of rays emitted by a radiation source.

It is desirable that the gain of the amplification section calculated by the gain calculation section be less than that at the time of the previous reading of the radiographic image.

It is desirable that the gain calculation section calculates the gain of the amplification section such that high and small gains are alternately repeated whenever the rereading is performed.

It is desirable that the gain of the amplification section calculated by the gain calculation section be a value equal to $(1/2)^n$ times the initial value where n is an integer other than 0.

It is desirable that the determination section determines whether or not performing the rereading is necessary, based on an appearance frequency distribution of pixel values in the synthesized radiographic image.

It is desirable that the determination section determines whether or not performing the rereading is necessary, based on an effective range that indicates a distribution of pixel values of pixels indicating the subject depending on the appearance frequency distribution.

It is desirable that the determination section extracts pixels belonging to the effective range, set an average value of pixel values of the extracted pixels as the evaluation value, and determine whether or not the rereading is necessary, by determining that the rereading is not necessary when the evaluation value is in the predetermined range and determining that the rereading is necessary when the evaluation value is outside of the predetermined range.

It is desirable that the determination section sets an average value between a maximum value and a minimum value of the effective range as the evaluation value, and determines whether or not performing the rereading is necessary.

It is desirable that the determination section sets an amount of deviation between a width of the effective range and a predetermined width as the evaluation value, and determines whether or not performing the rereading is necessary.

It is desirable that when determining that the rereading is necessary, the determination section further evaluates an amount of noise of the synthesized radiographic image, and determine the number of times the rereading is performed.

It is desirable that the determination section evaluate graininess of the synthesized radiographic image as the amount of noise.

It is desirable that the determination section evaluate the amount of noise based on the synthesized radiographic image generated from the radiographic image, which is read first, and the radiographic image which is read second.

Further, according to the present invention, there is provided a radiographic imaging system including: a radiation source; and the radiographic imaging apparatus that receives radiation, which is emitted from the radiation source and transmitted through a subject.

Furthermore, according to the present invention, there is provided a radiographic imaging method including: a signal electric charge accumulation step of accumulating signal electric charges corresponding to amounts of radiation, which is emitted onto a subject and is incident into a plurality of pixels, through a radiographic image detection section having the plurality of pixels, which receives the radiation and detects a radiographic image, and being capable of nondestructively reading data, which indicates the radiographic image, from the pixels; a radiographic image reading step of reading the radiographic image by amplifying signals corresponding to the signal electric charges through an amplification section which is capable of amplifying the signals and is capable of varying gain used for reading the radiographic image when the radiographic image is read from the radiographic image detection section; an image synthesis step of outputting the radiographic image, which is read first by the radiographic image detection section, as a synthesized radiographic image when the radiographic image is read first, and synthesizing a plurality of the radiographic images, which are read from the radiographic image detection section through the rereading, so as to generate a synthesized radiographic image when the plurality of the radiographic images is read; a rereading necessity determination step of obtaining an evaluation value for evaluating the radiographic image based on pixel values in a whole region of the radiographic image, and determining whether or not performing a rereading of the radiographic image is necessary based on the evaluation value; a gain calculation step of calculating a new gain of the amplification section used at the time of the rereading based on the evaluation value when it is determined that the rereading is necessary from a result of the determination as to whether or not performing the rereading; a rereading step of changing the gain of the amplification section to the calculated gain and rereading the radiographic image using the changed gain; and a second image synthesis step of generating a new synthesized radiographic image including the new radiographic image which is obtained through the rereading.

According to the present invention, it is possible to reliably obtain a radiographic image with good image quality, without overflow or underflow, even when the dosing amount is small, in the radiography.

BRIEF DESCRIPTION OF THE DRAWINGS

FIG. 18 is a flowchart illustrating another aspect in which the number of rereading operations is set in advance.

DESCRIPTION OF THE PREFERRED EMBODIMENTS

First Embodiment

Figure 1:
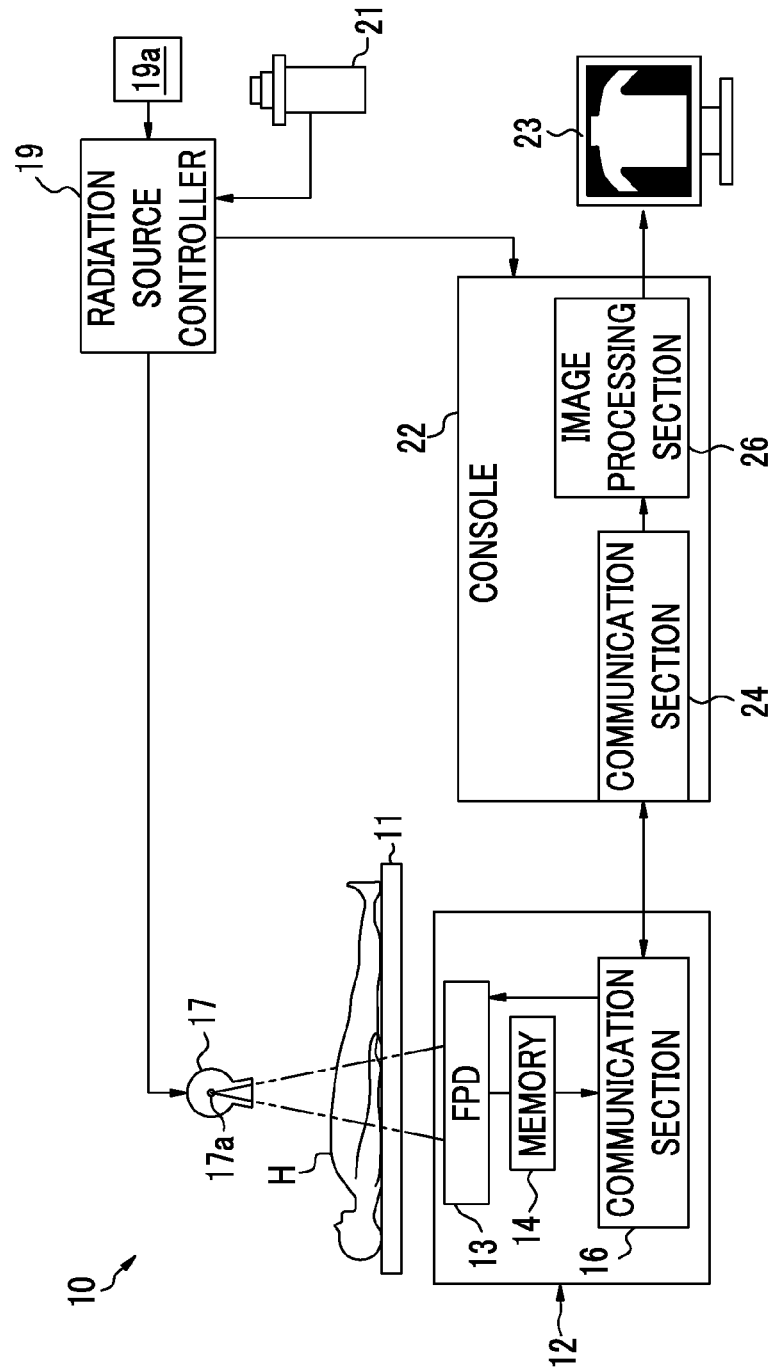
FIG. 1 is an explanatory diagram schematically illustrating a configuration of an X-ray imaging system.

As shown in FIG. 1, an X-ray imaging system 10 includes an imaging stage 11, an electronic cassette (radiographic image detection device) 12, an X-ray source 17, a radiation source controller 19, a console 22, a monitor 23, and the like. The X-ray source 17 and the radiation source controller 19 constitute an X-ray generator. The electronic cassette 12, the console 22, and the monitor 23 constitute an X-ray imaging apparatus (radiographic imaging apparatus).

A subject H is placed on the imaging stage 11, and the electronic cassette 12 is set on the imaging stage 11 or between the imaging stage 11 and the subject H such that X-rays transmitted though the subject H are incident thereto.

The electronic cassette 12 is detachably provided on the imaging stage 11, and is a portable type which is usable even when the imaging stage 11 is not used, and is provided with an FPD 13, various circuits that control operations of the FPD 13, a memory 14, a communication section 16, and the like, in a casing having a substantially rectangular parallelepiped shape. The FPD 13 has pixels arranged in a matrix, and detects an X-ray image by accumulating signal electric charges corresponding to the amount of incident X-rays in the respective pixels, converting the accumulated signal electric charges into voltage signals, and outputting the signals. Further, the FPD 13 is a CMOS type capable of nondestructive reading. The memory 14 temporarily stores the X-ray image which is output by the FPD 13. The communication section 16 communicates control signals to the console 22, and transmits the X-ray image, which is stored in the memory 14, to the console 22. Further, the electronic cassette 12 is a wireless type which has a built-in battery (not shown) for feeding power to the respective sections such as the FPD 13, and the communication section 16 performs wireless communication with the console 22 through, for example, radio waves or light such as infrared rays.

The X-ray source 17 has an X-ray tube that generates X-rays and a collimator that restricts irradiation of X-rays, and emits X-rays toward the subject H from an X-ray focal point 17a. The X-ray source 17 is provided to be movable relative to the imaging stage 11, and thus it is possible to freely adjust an angle or an irradiation position of the X-rays. Further, the X-ray source 17 is connected to the radiation source controller 19. The radiation source controller 19 is provided with a high voltage generation section that supplies electric power to the X-ray source 17, and causes emission of the X-rays from the X-ray source 17 by applying a tube voltage and tube current corresponding to the imaging conditions, which are input to the radiation source controller 19, to the X-ray source 17.

The radiation quality of the X-rays is determined depending on the tube voltage, and the dosing amount thereof is determined depending on the tube current and the irradiation time. The radiation source controller 19 is provided with an operation panel 19a, and receives an input of imaging conditions, which includes the tube voltage, the tube current, and the irradiation time of the X-ray tube, through the operation panel. The imaging conditions are determined by an imaging target portion, the physical size and the age of a subject, and the like. Further, the radiation source controller 19 is connected to an irradiation switch 21 that inputs an irradiation start signal. The radiation source controller 19 is connected to the console 22 of the X-ray imaging apparatus so as to be able to communicate therewith, and synchronizes the electronic cassette 12 and the X-ray source 17 by communicating with the console 22.

Figure 2:
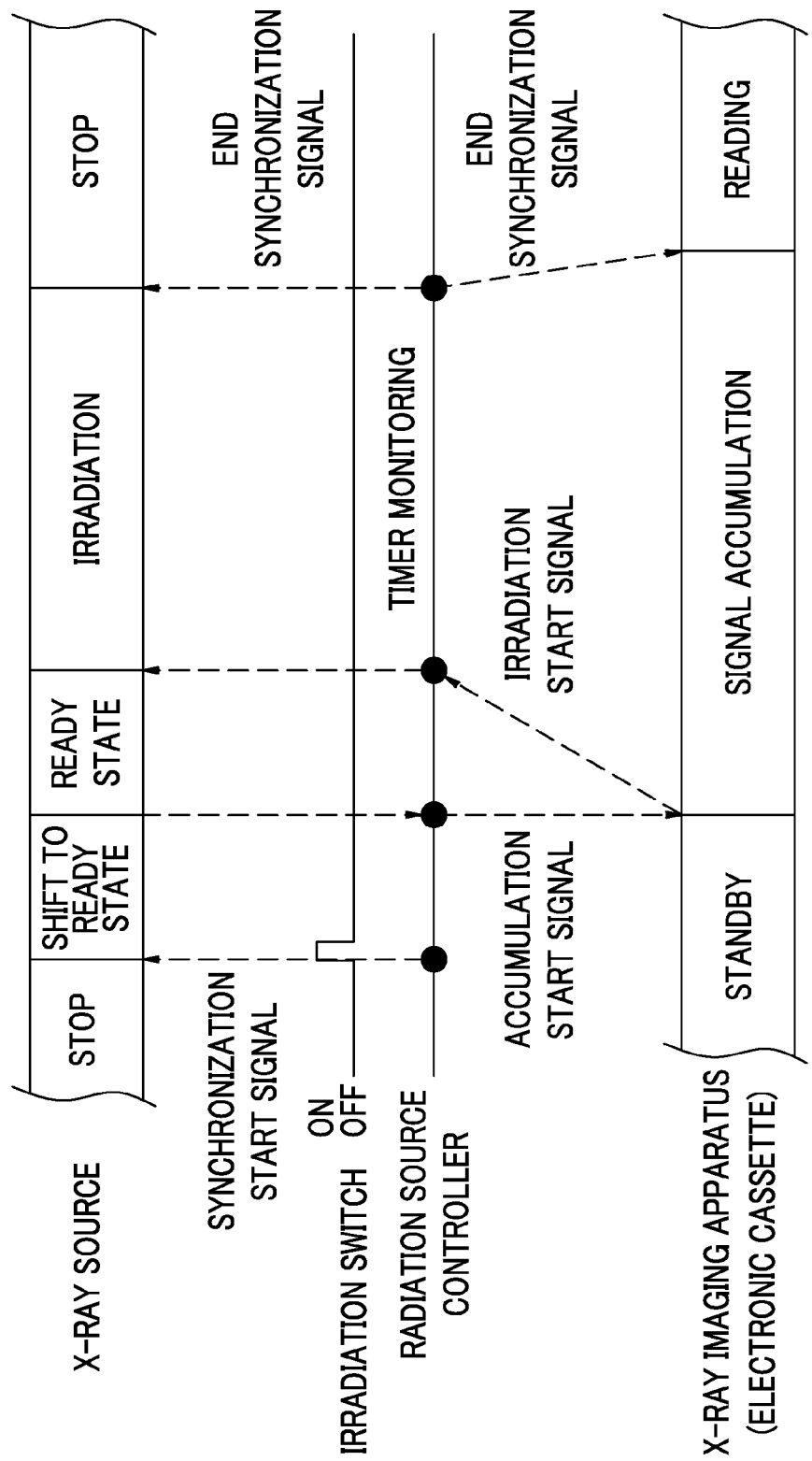
FIG. 2 is an explanatory diagram illustrating a sequence of synchronization between an electronic cassette and an X-ray source.

As shown in FIG. 2, the radiation source controller 19 detects the synchronization start signal and starts an operation such as filament heating of the X-ray tube or rotation of a target if the irradiation switch 21 is pressed down and turned on, and shifts the X-ray source 17 to an irradiation possible state (hereinafter referred to as a ready state). When the X-ray source 17 is in the ready state, the radiation source controller 19 transmits an accumulation start signal to the console 22. When receiving the accumulation start signal, the console 22 shifts the electronic cassette 12 from a standby operation to an accumulation operation for accumulating the signal electric charge. When the electronic cassette 12 shifts to the accumulation operation, the irradiation start signal is transmitted to the radiation source controller 19. When receiving the irradiation start signal, the radiation source controller 19 starts irradiation of the X-rays of the dosing amount and the radiation quality according to the imaging conditions from the X-ray source 17 toward the subject H by supplying the X-ray source 17 with the electric power according to the tube voltage and the tube current which are set by the imaging conditions. The radiation source controller 19 starts measuring the irradiation time by activating a timer after the start of the irradiation of the X-rays.

The radiation source controller 19 monitors the timer. If the irradiation time set by the imaging conditions has elapsed, the controller sends an end synchronization signal to the X-ray source 17, and ends the irradiation. Further, the radiation source controller 19 transmits the end synchronization signal to the console 22. When receiving the end synchronization signal, the console 22 shifts the electronic cassette 12 from the accumulation operation to a reading operation.

In FIG. 1, the console 22 is a controller that controls an operation of the electronic cassette 12 by transmitting the control signal through the communication section 24, and is connected to the irradiation switch 21 and an input device such as a keyboard or a mouse, not shown. The console 22 receives an input of the same imaging conditions as that of the radiation source controller 19 in advance by using, for example, the input device.

The console 22 is connected to medical information systems such as a hospital information system (HIS) and a radiation information system (RIS) (not shown) so as to be able to communicate therewith, and may receive an imaging order of X-ray imaging from the medical information system. An operator such as a doctor or a clinical radiologist checks the subject information and the imaging target portion in the received imaging order, determines the imaging conditions appropriate thereto, and inputs the imaging conditions to each of the X-ray control section 19 and the console 22, thereby setting the imaging conditions. The imaging conditions, which are input to the console 22, are set in the electronic cassette 12. The set imaging conditions are used in setting an initial value of the gain of the amplifier as described later.

The X-rays, which are emitted from the X-ray source 17 and transmitted through the subject H, are incident into the electronic cassette 12. The electronic cassette 12 accumulates the signal electric charges corresponding to the amounts of incident X-rays in the accumulation operation, thereby detecting the X-ray image that indicates the subject H. In the reading operation, the X-ray image corresponding to the signal electric charges accumulated is read. The read X-ray image is transmitted to the console 22 through the communication section 24.

The console 22 is provided with an image processing section 26. The image processing section 26 applies various kinds of image processing to the received X-ray image, and gives an output thereof to the monitor 23. Examples of the image processing, which is performed by the image processing section 26, include defect correction processing and offset processing. The defect correction processing is processing of correcting pixel values of defect pixels, from which it is difficult to obtain the pixel values depending on the amounts of emitted X-rays, through interpolation or the like. The offset processing is image processing of removing noise due to dark current and the like by subtracting the X-ray image (offset image), which is captured in advance in a state where there is no subject H, from the X-ray image which is obtained by capturing an image of the subject H. It should be noted that the image processing section 26 may perform image processing, such as synthesis processing of the X-ray image, other than the correction processing, as described later.

The monitor 23 displays the X-ray image, and additionally displays an operation screen for operating the console 22.

The console 22 adds the input imaging conditions as additional information to the processed X-ray image after ending of the image processing, and converts the image into a standard file format of a medical image file such as a Digital Imaging and Communication in Medicine (DICOM) format. The converted image file is transmitted to the storage device such as image server, not shown.

Figure 3:
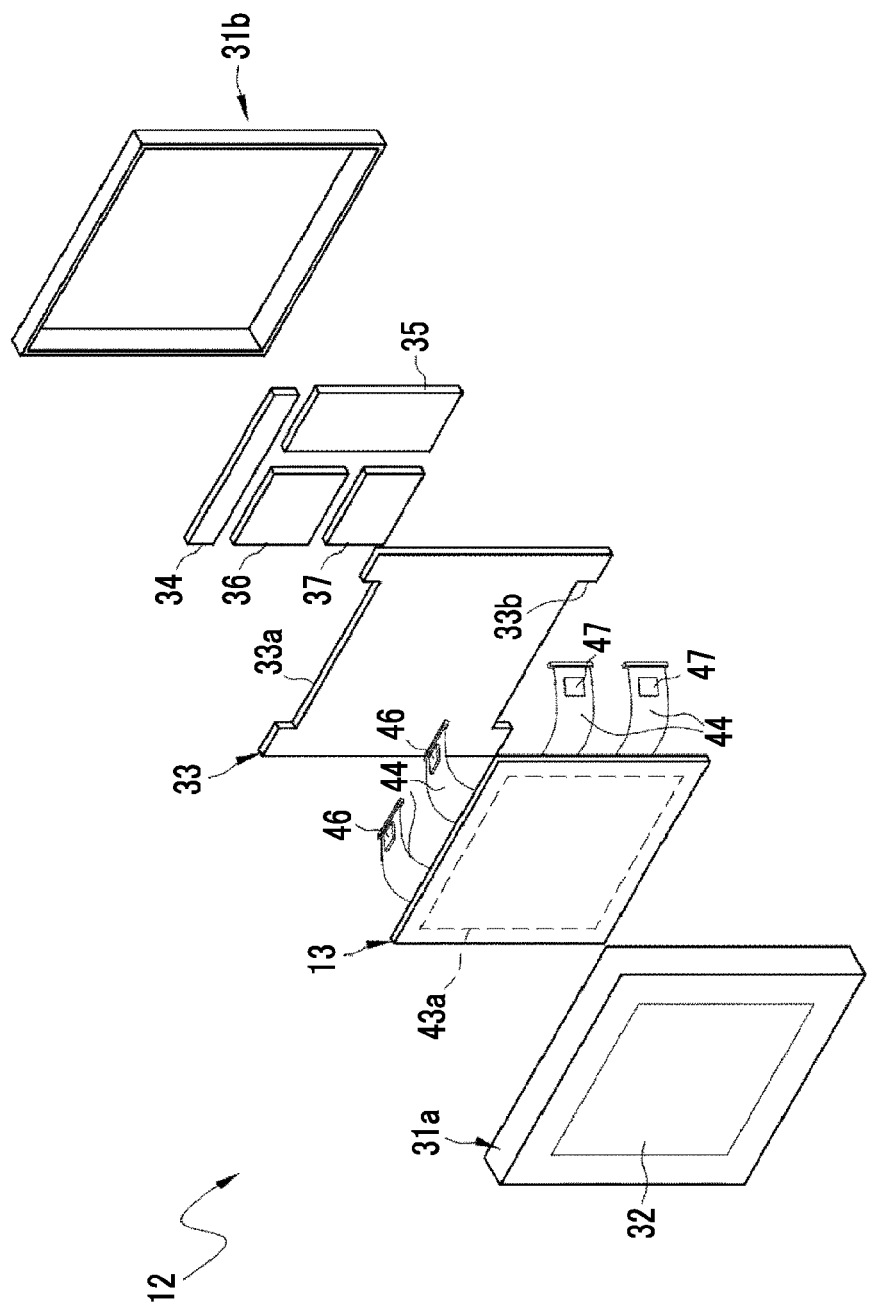
FIG. 3 is an exploded perspective view illustrating a configuration of the electronic cassette.
Figure 4:
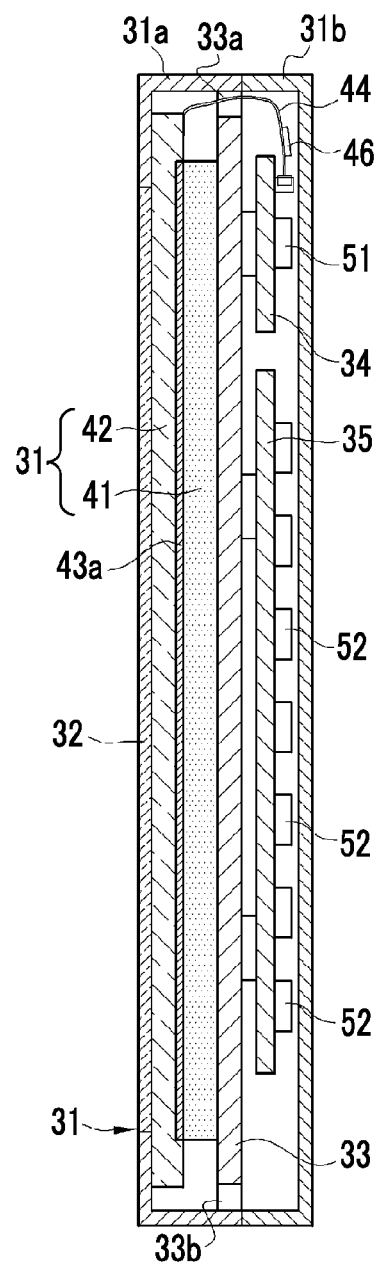
FIG. 4 is a cross-sectional view illustrating a configuration of the electronic cassette.

As shown in FIGS. 3 and 4, a casing 31 of the electronic cassette 12 is formed of a front cover 31a that covers the FPD 13 from the incident surface side onto which the X-rays are incident, and a rear cover 31b that covers the FPD 13 from the rear side. Both of the front cover 31a and the rear cover 31b are formed of a metal material (such as stainless steel) with a low X-ray transmittance. Here, the front cover 31a is provided with an X-ray transmission window 32, which is made of carbon with a high X-ray transmittance, such that the X-rays are incident into the FPD 13. In the casing 31, in order from the front cover 31a side, the FPD 13, a supporting body 33, and various circuit boards 34 to 37 that perform the operation control of the FPD 13 and the like are disposed.

The FPD 13 is an indirect conversion type formed of a scintillator 41 and an image sensor 42. The scintillator 41 is a fluorescent substance that emanates visible light with a light amount corresponding to the amount of incident X-rays, and is made of, for example, thallium activated cesium iodide (CsI:Tl), gadolinium oxysulfide (GOS), or the like. The image sensor 42 is a device that photoelectrically converts the visible light which is emitted by the scintillator 41, and is a unit in which an area of a detection surface 43a is increased by assembling a plurality of CMOS sensor chips formed of, for example, a single silicon substrate. The detection surface 43a, on which the pixels for performing photoelectric conversion are arranged, is disposed to face the scintillator 41. Further, the FPD 13 is disposed between the front cover 31a and the supporting body 33 such that the image sensor 42 is disposed on the front cover 31a side and the scintillator 41 is disposed on the supporting body 33 side (rear cover 31b side). That is, the electronic cassette 12 is a rear irradiation type, and thus the FPD 13 is disposed such that the X-ray incidence side surface of the scintillator 41, on which the amount of emitted light is largest, faces the detection surface 43a. Incidentally, the scintillator 41 is bonded to the supporting body 33 and the image sensor 42, and the image sensor 42 is bonded to the scintillator 41 and the front cover 31a.

The supporting body 33 is provided on the rear side of the FPD 13 so as to divide the space in the casing 31 into two parts. On the rear side of the supporting body 33, the various circuit boards 34 to 37 are mounted. The supporting body 33 is made of, for example, stainless steel, and is fixed on the casing 31. Further, notches 33a and 33b are respectively formed on the center portions of the top and the bottom of the supporting body 33, and the flexible cable 44, which connects the various circuit boards 34 to 37 with the FPD 13, is inserted and passes therethrough. On the flexible cable 44, tape carrier package (TCP) type integrated circuit (IC) chips 46 and 47 are mounted.

The circuit board 34 is a driving circuit board on which the driving circuit 51 for driving the FPD 13 is formed. The circuit board 35 is an A/D (Analog/Digital) conversion circuit board on which the output circuit (refer to FIG. 5) including an A/D conversion circuit 52 is formed. The A/D conversion circuit 52 converts an analog signal, which is output by an IC chip 47 to be described later, into a digital signal. The circuit board 36 is a board on which the memory 14, a control section 61, and a rereading determination section 66 (refer to FIG. 5) are formed. The control section 61 controls the respective sections of the FPD 13, and controls communication with the console 22. The circuit board 37 is a power supply circuit board on which the power supply circuit is formed. The power supply circuit is a circuit that supplies electric power to the respective sections, and has circuit elements such as an AC/DC (Alternating current/Direct current) converter, which converts alternating current into direct current, and a DC/DC converter which converts direct current voltage into a voltage necessary for an operation of each circuit.

Figure 5:
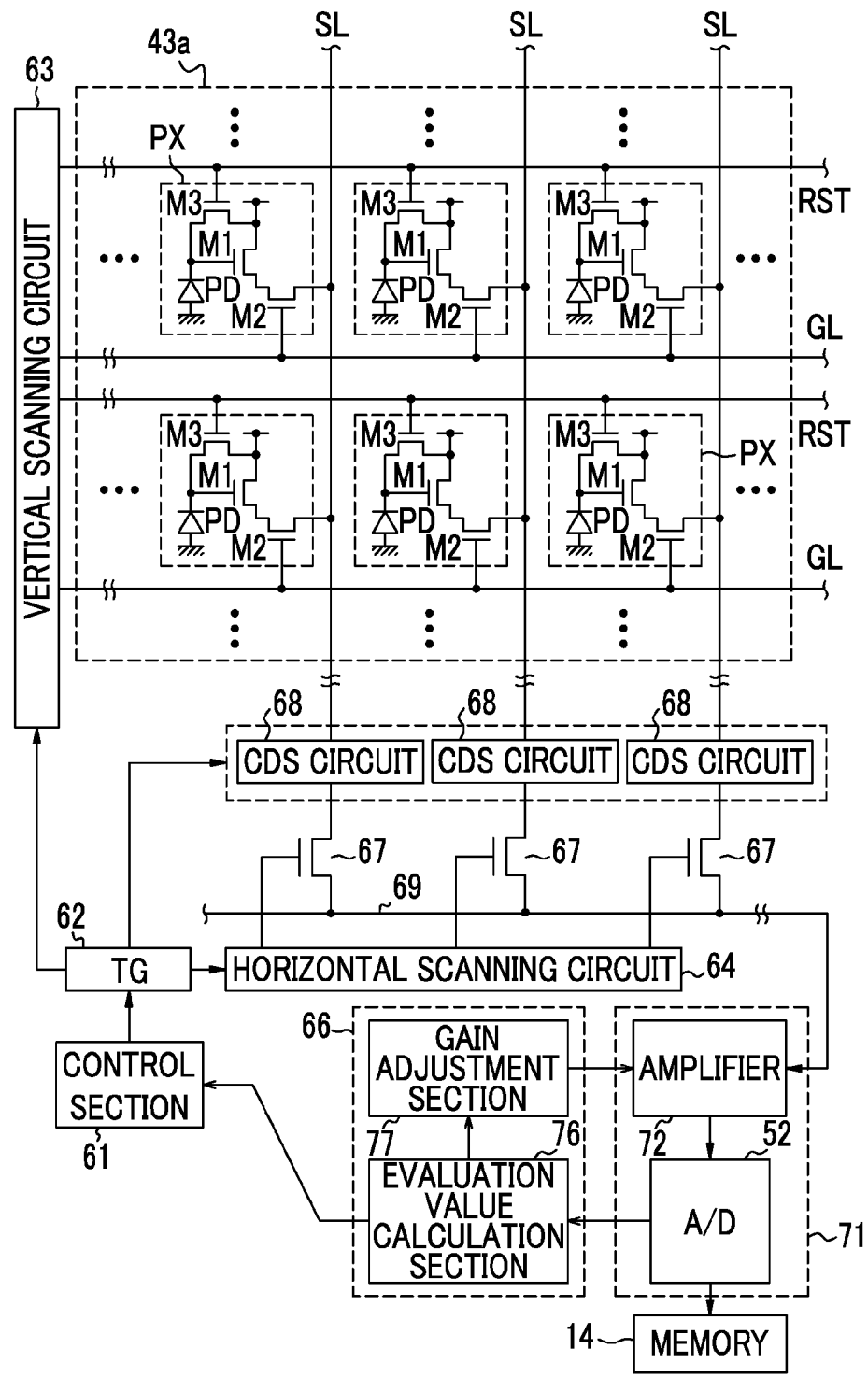
FIG. 5 is an explanatory diagram illustrating a configuration of an FPD.

The IC chip 46 is amplifiers and shift registers constituting the driving circuit 51 together with the circuit elements formed on the circuit board 41, and includes a vertical scanning circuit 63 (refer to FIG. 5). The IC chip 47 is an application specific integrated circuit (ASIC) constituting a reading circuit formed of a CDS circuit 68 (refer to FIG. 5) to be described later.

As shown in FIG. 5, each pixel PX of the FPD 13 is formed of a photodiode PD and transistors M1 to M3, and performs an accumulation operation, a reading operation, and a reset operation, in accordance with driving states of the respective transistors M1 to M3. The accumulation operation is an operation that accumulates the signal electric charge which is generated by photoelectric conversion, and the reading operation is an operation that outputs a voltage signal corresponding to the amount of the accumulated signal electric charge. The reset operation is an operation that drains the accumulated signal electric charge.

The photodiode PD is an element that generates a signal electric charge corresponding to the amount of light incident from the scintillator 41 through photoelectric conversion, and is connected to a gate electrode of an amplification transistor M1 and a source electrode of a reset transistor M3. In the case where the signal electric charge is accumulated and the case where the voltage signal is read from the pixel PX, the reset transistor M3 is turned off, and a voltage corresponding to the amount of the signal electric charge accumulated in the photodiode PD is applied to the gate electrode of the amplification transistor M1.

A power supply voltage is applied to a source electrode of the amplification transistor M1, and a pixel selection transistor M2 is connected to a drain electrode thereof. Thereby, a voltage corresponding to the amount of the signal electric charge applied to the gate electrode thereof is amplified with a predetermined amplification ratio, and is applied to a source electrode of the pixel selection transistor M2. A gate electrode of the pixel selection transistor M2 is connected to a row selection line GL, and a drain electrode thereof is connected to a signal line SL. Thereby, when a gate signal is input from the row selection line GL, a voltage of the source electrode thereof is output to the signal line SL. Thereby, a voltage signal of the pixel PX is read through the signal line SL. In addition, the FPD 13 is a CMOS type capable of nondestructive reading. Hence, even when the voltage signal is read from the pixel PX, each pixel PX retains the signal electric charge until the reset is performed.

When the signal electric charge accumulated in the photodiode PD is drained, the reset transistor M3 is turned on. A gate electrode of the reset transistor M3 is connected to a reset line RST, and a reset signal is input through the reset line RST. When the reset transistor M3 is turned on in response to the input of the reset signal, the pixel PX at the row drains the signal electric charge accumulated in the photodiode PD into the drain electrode side of the reset transistor M3.

Further, the FPD 13 includes a control section 61, a timing generator (TG) 62, a vertical scanning circuit 63, a horizontal scanning circuit 64, a rereading determination section 66, and the like.

The control section 61 integrally controls the respective sections of the FPD 13. The TG 62 generates a timing signal based on an instruction issued from the control section 61. The vertical scanning circuit 63 and the horizontal scanning circuit 64 are operated based on a clock signal which is input from the TG 62.

The vertical scanning circuit 63 is a driving circuit for the pixels PX, and causes the pixels PX to perform an accumulation operation, a reading operation, or a reset operation by selecting a row of the driven pixels PX and inputting the gate signal and the reset signal to the reset line RST or the row selection line GL of the selected row. The horizontal scanning circuit 64 is a circuit that selects a column of the pixels PX on which the reading of the voltage signal is performed, and selects a column on which the reading is performed by turning on one of column selection transistors 67 provided on the respective signal lines SL.

The row selection line GL is a line for inputting the gate signal, which controls operations of the pixels PX, from the vertical scanning circuit 63, and is provided for each row of the pixels PX. Based on the gate signal which is input through the row selection line GL, the pixel PX performs the accumulation operation or the reading operation. The reset line RST is a line for inputting the reset signal to the pixels PX, and is provided for each row of the pixels PX. The pixels PX in the reset line RST, to which the reset signal is input, are reset by draining the signal electric charges.

The signal line SL is a line for reading the voltage signal (imaging signal) corresponding to the amount of the signal electric charge from each pixel PX, and is provided for each column of the pixels PX. Further, the end of the signal line SL is connected to a correlation double sampling (CDS) circuit 68 and a column selection transistor 67. The CDS circuit 68 operates based on the clock signal which is input from the TG 62, and samples and retains the voltage signals so as to remove noise, which is caused at the reading, from the pixels PX in the row selection line GL which is selected by the vertical scanning circuit 63. The voltage signals, which are retained by the CDS circuit 68, are input to an output circuit 71 through an output bus line 69 by turning on the column selection transistors 67 through the horizontal scanning circuit 64.

The output circuit 71 includes an amplifier 72 and the A/D conversion circuit 52. The amplifier 72 amplifies the voltage signals which are input from the CDS circuit 68, and inputs the signals to the A/D conversion circuit 52. The A/D conversion circuit 52 converts the voltage signals, which are amplified by the amplifier 72, into digital data. The digital data, which is output from the A/D conversion circuit 52, is temporarily stored as an X-ray image in the memory 14, and is transmitted to the console 22 through the communication section 16. The amplifier 72 is a variable gain amplifier capable of freely adjusting the gain. In the reading operation, the gain is set to a predetermined value (initial value $\gamma_0$) based on the imaging conditions at the first reading of the X-ray image, and is set to a new value by a gain adjustment section 77 in a case of rereading the X-ray image. Further, data, which is output from the output circuit 71, is stored in the memory 14 as described above, and is input to the rereading determination section 66.

The rereading determination section 66 is formed of an evaluation value calculation section 76 and the gain adjustment section 77. The evaluation value calculation section 76 calculates an evaluation value from the data, which is input from the output circuit 71, by acquiring pixel values of all pixels of the captured X-ray image, and determines whether or not the rereading is necessary. The calculation of the evaluation value depends on histogram analysis of the X-ray image as described later.

Figure 6:
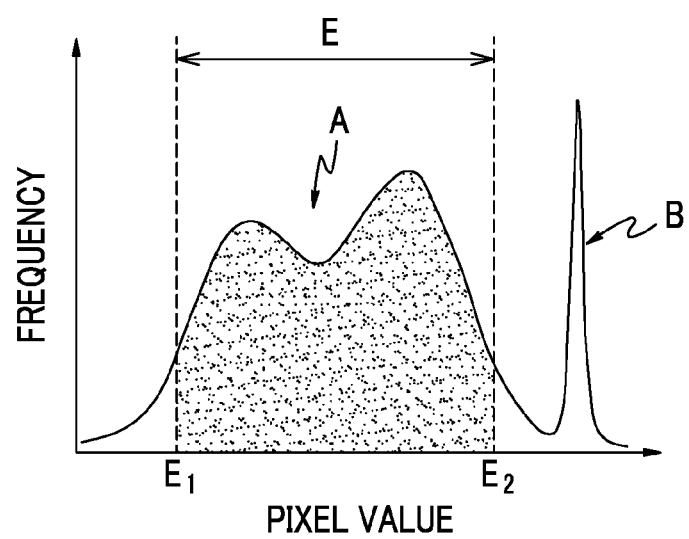
FIG. 6 is a graph schematically illustrating a frequency distribution of pixel values.

As shown in FIG. 6, first, a distribution of the pixel values of all the pixels is obtained. The aspect of the distribution of the pixel values has a substantially regular distribution shape in accordance with an imaging target portion (head, chest, abdomen, etc.) without depending on the gain of the amplifier 72. FIG. 6 shows, as an example, a frequency distribution of the pixel values in the case of the X-ray image of the chest of an adult. The distribution A with two peaks indicates a region of the chest tissue (lungs, heart, ribs, etc.), and the distribution B indicates pixels (so-called bypassed pixels) through which the most of the X-rays directly reach the detection surface 43a without being transmitted through the subject H.

The evaluation value calculation section 76 extracts pixels belonging to an effective range E, which is a predetermined region, from the frequency distribution of the pixel values. The effective range E, which is a predetermined region, is determined in advance relative to the distribution shape of the pixel values corresponding to the imaging target portion. Specifically, the range is determined in advance in the frequency distribution so as to include pixels indicating some tissues as main observation targets. For example, in a case of chest X-ray imaging, lungs, ribs, and the like are main observation targets, and the effective range E is determined in advance relative to the frequency distribution of the pixel values so as to include pixels indicating portions such as lungs or ribs and so as not to include other unnecessary pixels such as bypassed pixels of the distribution B.

When the gain of the amplifier 72 is small, the frequency distribution of the pixel values as shown in FIG. 6 is shifted as a whole to the left side. On the contrary, when the gain of the amplifier 72 is large, the distribution is shifted as a whole to the right side. However, as described above, the distribution shape itself is substantially invariable in accordance with the imaging target portion. Hence, it is possible to extract pixels, which belongs to the effective range E and indicate main observation targets, from the frequency distribution of the pixel values in the read X-ray image. It is apparent that, depending on the gain of the amplifier 72 at the time of reading the X-ray image, the values of the maximum value $E_2$ and the minimum value $E_1$ of the effective range E are different.

Figure 7:
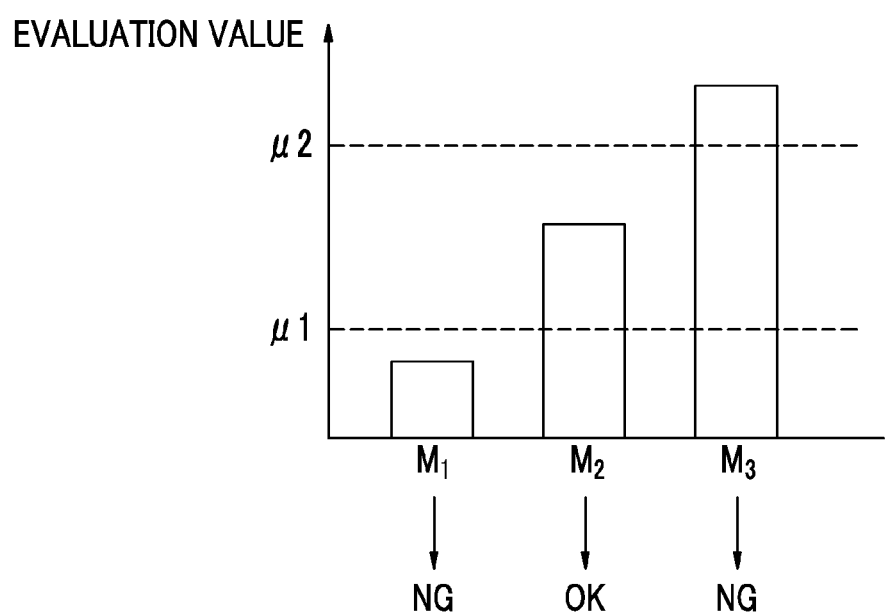
FIG. 7 is an explanatory diagram of a rereading determination method.

The evaluation value calculation section 76 calculates an average value of the pixel values of the pixels belonging to the extracted effective range E, and sets the average value as the evaluation value M which is used to determine whether or not the rereading is necessary. Then, as shown in FIG. 7, comparing the evaluation value M with a small threshold value $\mu_1$ and a large threshold value $\mu_2$ which define the lower limit and the upper limit of an appropriate range, based on whether or not the evaluation value M is in the appropriate range, it is determined whether or not the rereading is necessary. Specifically, in FIG. 7, as in an evaluation value $M_2$, if the evaluation value M is equal to or greater than the small threshold value $\mu_1$ and equal to or less than the large threshold value $\mu_2$ ($\mu_1 < M < \mu_2$), it is determined that the rereading is not necessary (OK). In contrast, as in an evaluation value $M_1$, if the evaluation value M is smaller than the small threshold value $\mu_1$ ($\mu_1 > M$), or, as in an evaluation value $M_3$, if the evaluation value M is greater than the large threshold value $\mu_2$ ($M > \mu_2$), it is determined that the rereading is necessary (NG). The reason is as follows. If the evaluation value M is less than the small threshold value $\mu_1$, the gain of the amplifier 72 is excessively small, and thus underflow occurs. If the evaluation value M is greater than the large threshold value $\mu_2$, the gain of the amplifier 72 is excessively large, and thus overflow occurs. As a result, the read X-ray image is inappropriate for observation of the subject H. Specific values of the small and large threshold values $\mu_1$ and $\mu_2$ relative to the evaluation value M are determined such that no overflow or underflow occurs in the subject H (at least the main observation targets in the subject H).

If it is determined that it is necessary to reread the X-ray image, the evaluation value calculation section 76 inputs the calculated evaluation value M to the gain adjustment section 77, and inputs a rereading instruction to the control section 61. When receiving the rereading instruction from the evaluation value calculation section 76, the control section 61 controls the respective sections so as to perform the operation for reading the X-ray image again.

If it is determined that the rereading is necessary by the evaluation value calculation section 76, the gain adjustment section 77 calculates a value of the gain of the amplifier 72 at the time of the rereading based on the evaluation value M which is input from the evaluation value calculation section 76, and resets the gain of the amplifier 72. Hence, the rereading of the X-ray image, which is performed by inputting the rereading instruction issued from the evaluation value calculation section 76 to the control section 61, is performed based on a new gain which is reset by the gain adjustment section 77. It is the same for the case where the rereading is performed multiple times, and whenever the rereading is performed, the gain adjustment section 77 calculates a value of the new gain, and resets the gain of the amplifier 72 to the calculated value.

Specifically, at the time of determining whether or not the rereading is necessary in the evaluation value calculation section 76, if the evaluation value M is less than the small threshold value $\mu_1$ ($\mu_1 > M$), the gain of the amplifier 72 at the time of the rereading is reset to a value $\gamma_2$ ($\gamma_0 < \gamma_2$) greater than the initial value $\gamma_0$ by the gain adjustment section 77. In contrast, if the threshold value M is greater than the large threshold value $\mu_2$ ($M > \mu_2$), the gain of the amplifier 72 at the time of the rereading is reset to a value $\gamma_1$ ($\gamma_0 > \gamma_1$) less than the initial value $\gamma_0$ by the gain adjustment section 77. The initial value $\gamma_0$ of the gain of the amplifier 72 is determined by the imaging conditions as described above.

Hereinafter, an effect of the X-ray imaging system 10 configured as described above will be described with reference to the flowchart shown in FIG. 8.

Figure 8:
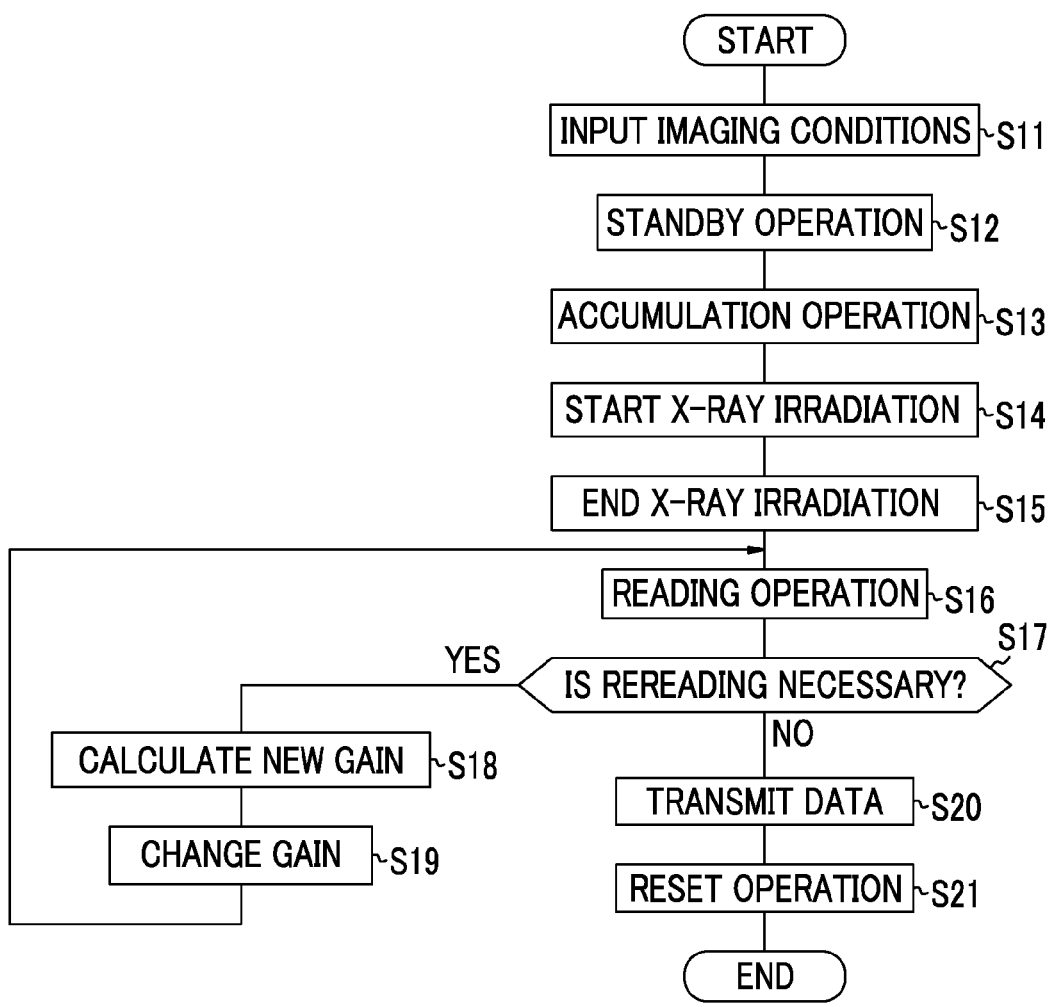
FIG. 8 is a flowchart illustrating an effect of the X-ray imaging system.

As shown in FIG. 8, when the X-ray imaging system 10 performs the X-ray imaging, first, the imaging conditions are input to the radiation source controller 19 and the console 22 (step S11). The radiation source controller 19 receives inputs of the tube voltage, the tube current, the irradiation time of the X-ray tube as the imaging conditions. The imaging conditions, which are input to the radiation source controller 19, are determined by the imaging target portion, the physical size and the age of the subject H, and the like which are confirmed by the imaging order received by the console 22.

The imaging conditions, which are input to the console 22, are transmitted to the electronic cassette 12 through the communication section 24. The electronic cassette 12 starts a standby operation when the imaging conditions are input from the console 22 (step S12). The standby operation is an operation that waits for start of irradiation of X-rays by repeating the reset operation at predetermined timing.

When the irradiation switch 21 is pressed, the synchronization start signal is transmitted to the X-ray source 17 through the radiation source controller 19, and the X-ray source 17 is shifted to a ready state. When the X-ray source 17 is in the ready state, the radiation source controller 19 transmits the accumulation start signal to the console 22, and the electronic cassette 12 starts the accumulation operation (step S13).

Further, when the electronic cassette 12 shifts to the accumulation operation, the radiation source control section 19 receives the irradiation start signal from the console 22, and starts irradiation of X-rays by using the tube voltage and the tube current corresponding to the imaging conditions from the X-ray source 17 (step S14).

The radiation source controller 19 monitors the timer. If the irradiation time set by the imaging conditions has elapsed, the controller sends an end synchronization signal to the X-ray source 17, and ends the irradiation of X-rays (step S15). At the same time, the radiation source controller 19 transmits the end synchronization signal to the console 22, and the console 22 shifts the electronic cassette 12 from the accumulation operation to the reading operation (step S16). At the first reading (first time) in the reading operation, the gain of the amplifier 72 of the output circuit 71 is set to a predetermined value (initial value) $\gamma_0$ corresponding to the imaging conditions, and all pixels are nondestructively read in that state.

When the gain of the amplifier 72 is set to the initial value $\gamma_0$ and the first reading is completed, the X-ray image, which is obtained by the first reading, is converted into digital data by the A/D converter 52 and is temporarily stored in the memory 14. The data of the X-ray image, which is stored in the memory 14, is input to the evaluation value calculation section 76, whereby it is determined whether or not the rereading is necessary (step S17). The evaluation value calculation section 76 performs, as shown in FIG. 6, histogram analysis of the X-ray image, and calculates the evaluation value M. Then, as shown in FIG. 7, comparing the evaluation value M with predetermined small and large threshold values $\mu_1$ and $\mu_2$, it is determined whether or not the rereading is necessary.

If the evaluation value M is equal to or greater than the small threshold value $\mu_1$ and equal to or less than the large threshold value $\mu_2$ (the evaluation value M2 in FIG. 7), the evaluation value M is in the appropriate range. Therefore, the gain of the amplifier 72 at the time of reading the X-ray image is appropriate, and it is determined that the rereading is not necessary (OK). In this case, the X-ray image, which is stored in the memory 14, is transmitted to the console 16 through the communication section 16 (step S20). Further, by performing the reset operation, the signal electric charge accumulated in each pixel PX is drained (step S21). The X-ray image transmitted to the console 22 is subjected to various kinds of image processing such as defect correction processing and offset processing by the image processing section 26, and is displayed on the monitor 23, or transmitted to an image server (not shown). As described above, if the evaluation value calculation section 76 determines that the rereading is not necessary, the X-ray image is read only once with the gain (initial value $\gamma_0$) which is set based on the imaging conditions.

In contrast, as in a case where the evaluation value M is less than the small threshold value $\mu_1$ (in the case of the evaluation value M1 in FIG. 7), or as in a case where the evaluation value M is greater than the large threshold value $\mu_2$ (in the case of the evaluation value M3 in FIG. 7), if the evaluation value M is outside of the appropriate range, it is determined that the gain of the amplifier 72 at the time of the first reading of the X-ray image is less than or greater than an appropriate value. As a result, it is determined that the rereading is necessary after the gain is adjusted. In this case, the gain adjustment section 77 calculates a new gain based on the evaluation value M (step S18), and sets the gain of the amplifier 72 to the calculated new value (step S19). As in the evaluation value M1, the evaluation value M is less than the small threshold value $\mu_1$. Hence, if it is determined that the rereading is necessary, the new gain, which is calculated by the gain adjustment section 77, becomes the value $\gamma_2$ which is larger than the initial value $\gamma_0$. In contrast, as in the evaluation value M3, the evaluation value M is greater than the large threshold value $\mu_2$. Hence, if it is determined that the rereading is necessary, the new gain, which is calculated by the gain adjustment section 77, becomes the value $\gamma_1$ less than the initial value $\gamma_0$. When the gain of the amplifier 72 is reset by the gain adjustment section 77, the control section 61 control the respective sections, based on the rereading instruction which is input from the evaluation value calculation section 76, and performs the reading operation again.

The determination as to whether or not the rereading is necessary (S17), the calculation of the new gain (S18), the change in gain (S19), and the rereading (S16) are repeatedly performed until the evaluation value M calculated based on the data of the read X-ray image becomes equal to or greater than the small threshold value $\mu_1$ and equal to or less than the large threshold value $\mu_2$ (until the evaluation value is in the appropriate range). Then, when it is finally determined that the rereading is not necessary, the data of the read X-ray image is transmitted to the console 22 (step S20). Thereafter, by performing the reset operation, the signal electric charges retained in the pixels PX are drained (step S21). The X-ray image transmitted to the console 22 is subjected to various kinds of image processing such as defect correction processing and offset processing by the image processing section 26, and is displayed on the monitor 23, or transmitted to an image server (not shown).

As described above, in the reading operation, the X-ray imaging system 10 reads all the pixels of the X-ray image once, performs histogram analysis on the read X-ray image, and determines whether or not the rereading is necessary, based on the analysis result. If it is determined that the rereading is necessary, the rereading is performed by adjusting the gain of the amplifier 72 of the output circuit 71. Therefore, it is possible to obtain the X-ray image appropriate for the main observation targets of the subject H without overflow or underflow. Since the X-ray image is nondestructively read, even when the reading is performed multiple times, the signal electric charges are retained in the pixels. Hence, there is no useless irradiation of X-rays.

Further, in the X-ray imaging system 10, in the adjustment of the gain used at the time of reading the X-ray image, by not using the pixel values of the determination pixels distributed in the detection surface as in the existing system but using the pixel values of all the pixels within the detection surface, the gain is adjusted. Hence, it is possible to determine an appropriate value of the gain based on the amount of incident X-rays in which the physical size of the subject H, the imaging target portion, or the like is more precisely reflected. Therefore, as compared with the existing system, it is possible to perform more appropriate gain adjustment.

Since it is possible to appropriately perform the gain adjustment, even when the dosing amount is set to be low in the imaging conditions, it is possible to obtain the X-ray image with good image quality. Such an effect contributes to reduction in the amount of radiation exposure of the subject H.

Further, by adjusting the gain used at the time of reading the X-ray image, it is possible to obtain the X-ray image with better image quality, compared with a case of obtaining the X-ray image and thereafter adjusting a density of the X-ray image through the image processing such as gradation conversion processing. That is, in the case of using the image processing, it is difficult to improve the S/N (Signal to Noise ratio) to the noise caused by the ASIC such as the IC chip 47, but in the X-ray imaging system 10, the signal values are adjusted at the step of reading the signal sent from the FPD 13, and thus it is possible to obtain the X-ray image with good S/N and better image quality.

In the description of the analysis using the image histogram of the present example, the following example was given: the evaluation value calculation section 76 extracts pixels belonging to an effective range E, from the frequency distribution of the pixel values of the read X-ray image, and sets the average value of all the pixel values as the evaluation value M. However, the average value between the maximum value $E_2$ and the minimum value $E_1$ of the effective range E may be simply set as the evaluation value M. Alternatively, the evaluation value M may be acquired by using a partial region of the effective range E. For example, when the object of interest is a bone portion, the average value of the pixels corresponding to the bone portion in the effective range E may be set as the evaluation value M, or when the object of interest is a lung, the average value of the pixels corresponding to the lung in the effective range E may be set as the evaluation value M. Incidentally, the average value of all the pixels, which are not limited to the pixels in the effective range E and also includes the pixels of the bypass region, may be set as the evaluation value M. However, since the effective range E is a region that indicates the imaging target portion of the subject H, as described in the above example, it is desirable to use the pixel values belonging to the effective range E.

Further, the effective range E is changed by the gain of the amplifier 72. Specifically, when the gain is less than the appropriate value, the frequency distribution of the pixel values shown in FIG. 6 is shifted to the left side (negative side). In contrast, when the gain is greater than the appropriate value, the frequency distribution of the pixel values is shifted to the right side (positive side). Furthermore, the width of the frequency distribution is changed depending on the magnitude of the gain. Accordingly, by determining the width of the effective range E in advance in the case where the gain is the appropriate value and acquiring an amount of deviation between the width thereof and a width of the effective range E of the actually read X-ray image as the evaluation value M, the determination as to whether or not the rereading is necessary and the calculation of the new gain may be performed.

Second Embodiment

In the description of the above-mentioned first embodiment, the following example was given: by performing the rereading while changing the gain of the amplifier 72 until it is possible to obtain the X-ray image appropriate for observation of the subject H, only the X-ray image, which is finally read with an appropriate gain, is transmitted to the console 22. However, as described later in the second embodiment, by transmitting a plurality of the read X-ray images is transmitted to the console 22 while changing the gain of the amplifier 72 and by synthesizing the images, the X-ray image appropriate for observation of the subject H may be obtained. The second embodiment is the same as the first embodiment except the difference that a plurality of the X-ray images is synthesized. Accordingly, hereinafter, description will be given focusing on the difference. In addition, the common elements are represented by the same reference numerals and signs, and description thereof will be omitted.

Figure 9:
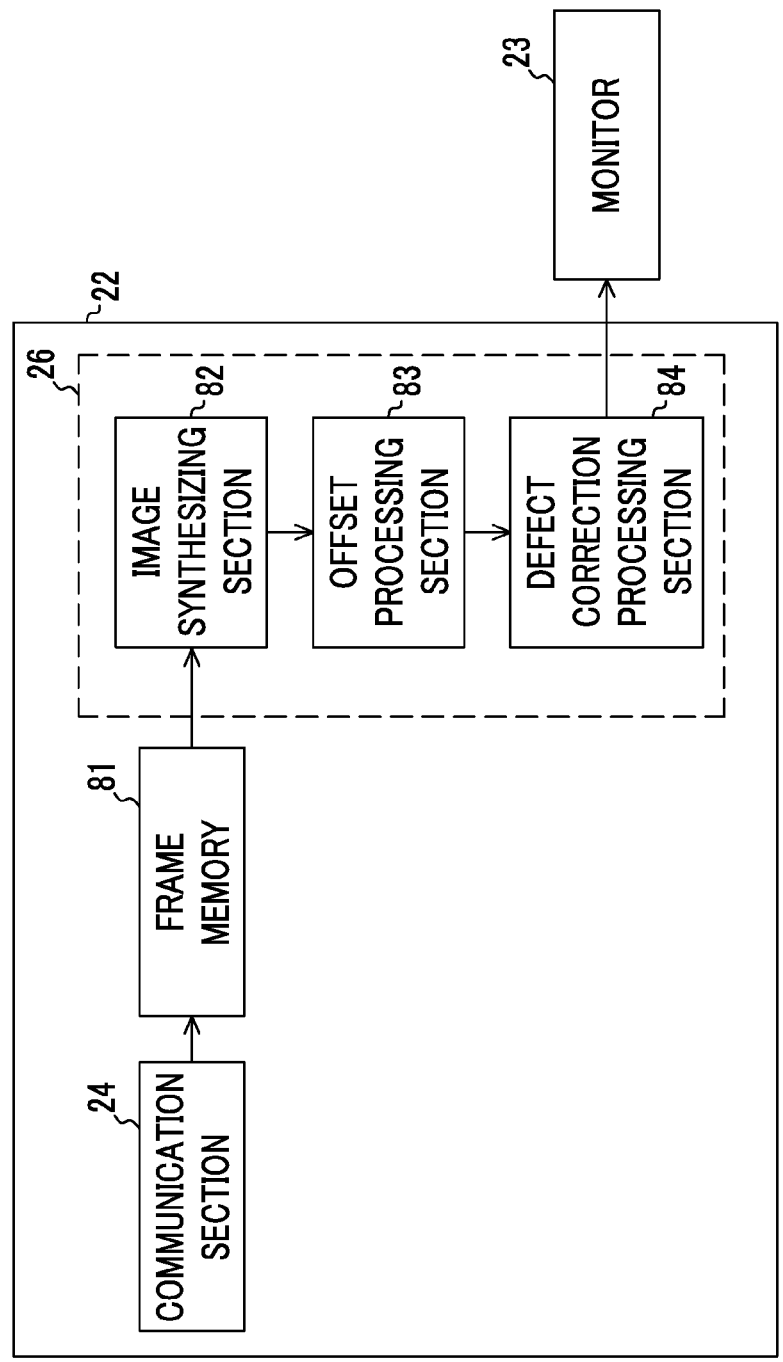
FIG. 9 is a block diagram illustrating a console according to a second embodiment.

In the second embodiment, first, the electronic cassette 12 performs the reading multiple times while changing the gain of the amplifier 72 in a similar manner to the above-mentioned first embodiment, but both X-ray images are transmitted to the console 22. Here, one is the X-ray image which is read with the gain of the initial value $\gamma_0$, and the other is the X-ray image of which the gain of the amplifier 72 has been changed through the rereading performed thereafter. Further, as shown in FIG. 9, in the console 22, there is provided a frame memory 81 that temporarily stores a plurality of X-ray images having different gains of the amplifier 72 at the time of the reading. In the image processing section 26, there is provided an offset processing section 83 that performs offset processing and a defect correction processing section 84 that performs defect correction. In addition, there is also provided an image synthesizing section 82 that synthesizes the plurality of X-ray images having different gains of the amplifier 72 at the time of the reading and generates a synthesized X-ray image appropriate for observation of the subject H.

Figure 10:
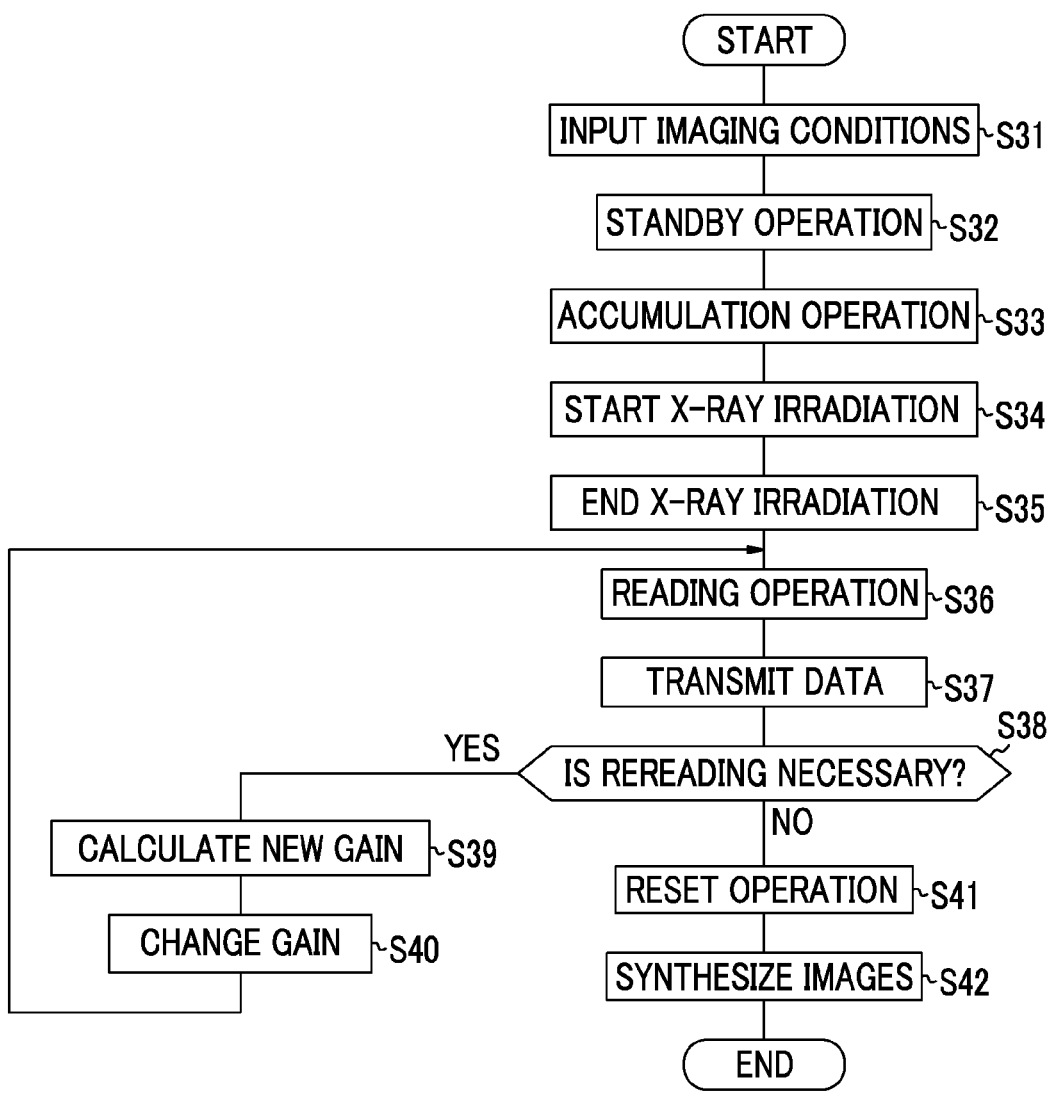
FIG. 10 is a flowchart illustrating an effect of the second embodiment.

As shown in the flowchart of FIG. 10, in the operation of the electronic cassette 12 of the second embodiment, when the imaging conditions are input (step S31), the electronic cassette 12 performs the standby operation (step S32). Then, when the irradiation switch 21 is pressed, the electronic cassette 12 starts the accumulation operation (step S33), and starts the irradiation of X-rays according to the set imaging conditions from the X-ray source 17 (step S34). When the irradiation of X-rays ends (step S35), the electronic cassette 12 performs the reading operation (step S36). At this time, the gain of the amplifier 72 is the initial value $\gamma_0$ which is determined in accordance with the imaging conditions. So far, the second embodiment is the same as the first embodiment.

In the second embodiment, the first X-ray image, which is read with the gain as the initial value $\gamma_0$, is temporarily stored in the memory 14, and is thereafter transmitted to the console 22, regardless of the result of determination as to whether or not the rereading is necessary (step S37). The console 22 temporarily stores the received X-ray image in the frame memory 81. Further, data of the first X-ray image is transmitted to the console 22, is input to the evaluation value calculation section 76, whereby it is determined, in the same sequence as the first embodiment, whether or not the rereading is necessary (step S38).

If the evaluation value calculation section 76 determines that the rereading is not necessary, the electronic cassette 12 performs the reset operation (step S41), and drains the signal electric charge accumulated in each pixel PX. Further, in the console 22, the image synthesizing section 82 acquires the X-ray image from the frame memory 81. However, since the input image is one, without the synthesis processing, the offset processing section 83 performs the offset processing, and the defect correction processing section 84 performs the defect correction processing, thereby displaying the image on the monitor 23.

In contrast, if the evaluation value calculation section 76 determines that the rereading is necessary, the gain adjustment section 77 calculates a new gain (step S39), changes the gain of the amplifier 72 into the calculation new gain (step S40). When the gain of the amplifier 72 is reset in such a manner, the electronic cassette 12 rereads the X-ray image (S36), temporarily stores the X-ray image, which is obtained with the new gain, in the memory 14, and thereafter transmits the image to the console 22. The calculation of the new gain and the resetting of the gain performed by the gain adjustment section 77 and the rereading at the new gain are performed until it is determined that the rereading is not necessary, in the determination as to whether or not the rereading is necessary by the evaluation value calculation section 76. However, all the X-ray images, which are obtained whenever the rereading is performed, are transmitted to the console 22.

By repeating the rereading while resetting the gain in such a manner, if it is finally determined that the rereading is not necessary, the electronic cassette 12 performs the reset operation (step S41), and drains the signal electric charge accumulated in each pixel PX. At the same time, in the console 22, the image synthesizing section 82 reads the plurality of X-ray images, which are read with different gains from the frame memory 81, and generates a synthesized X-ray image (step S42). The synthesized X-ray image, which is generated by the image synthesizing section 82, is subjected to the offset processing and the defect correction processing by the offset processing section 83 and the defect correction processing section 84, and is displayed on the monitor 23.

Figure 11:
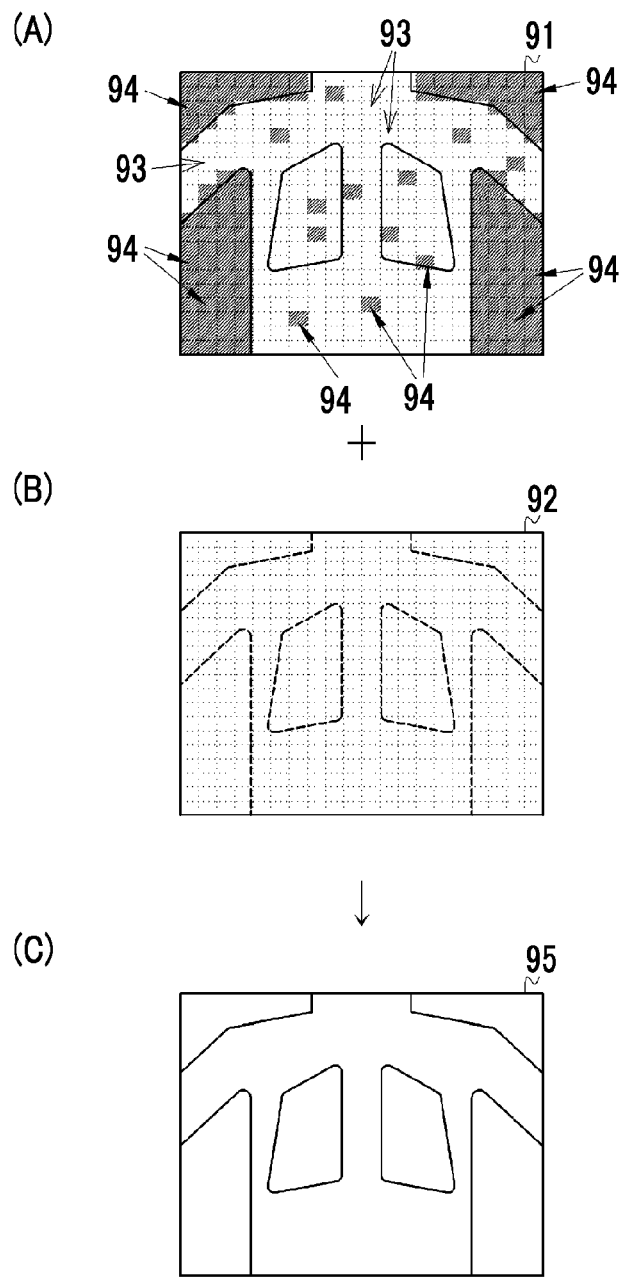
FIG. 11 is an explanatory diagram illustrating aspects of generation of a synthesized X-ray image.

The synthesized X-ray image is generated in the following manner. As described above, the frame memory 81 stores the plurality of X-ray images with respective different gains. However, for the sake of simplicity, it is assumed that the following two types of the X-ray images are obtained: one is a high-sensitive X-ray image 91 which is read with a high gain as shown in FIG. 11A; and the other is a low-sensitive X-ray image 92 which is read with a low gain as shown in FIG. 11B. In the high-sensitive X-ray image 91, there are pixels (hereinafter referred to as normal pixels) 93 with normal pixel values indicating the subject H and pixels (hereinafter referred to as saturated pixels) 94 of which the pixel values are saturated. The normal pixels 93 are pixels, of which the amounts of the signal electric charges are not saturated and do not reach the upper limit of the output of the amplifier 72, in the pixels PX of the FPD 13 and are pixels substantially indicating the subject H. In contrast, the saturated pixels 94 are pixels, of which the signal electric charges generated in the pixels PX of the FPD 13 are saturated, or pixels of which the signal electric charges reach the upper limit of the output of the amplifier 72 since the gain of the amplifier 72 is high even when the signal electric charges generated in the pixels PX of the FPD 13 are not saturated. Since the signal electric charges generated in the pixels PX of the FPD 13 are saturated, the pixels, which become the saturated pixels 94, are mostly bypassed pixels. However, reaching the upper limit of the output of the amplifier 72 since the gain is excessively high may occur even in the pixels indicating the subject H.

On the other hand, the low-sensitive X-ray image 92 is an image which is read in a state where the gain of the amplifier 72 is set to be low. Hence, in the image, at least the pixels, which indicate abnormal pixel values reaching the upper limit of the output of the amplifier 72 since the gain of the amplifier 72 is excessively high, are reduced. Here, in the low-sensitive X-ray image 92, as the gain at the time of the reading is low, all the pixels including the bypassed pixel indicate normal pixel values, and thus it is assumed that there is no pixel (no underflow) with a pixel value which is too low to contribute to resolution of the image. However, since the gain of the amplifier 72 at the time of the reading is low, the S/N thereof is worse than that of the high-sensitive X-ray image 91.

When the high-sensitive X-ray image 91 and the low-sensitive X-ray image 92 are obtained, the image synthesizing section 82, first, specifies positions of the saturated pixels 94 of the high-sensitive X-ray image 91, and extracts the normal pixels 93 of the high-sensitive X-ray image 91. Thereafter, from the low-sensitive X-ray image 92, the pixels, which are at the same positions as the saturated pixels 94 extracted from the high-sensitive X-ray image 91, are extracted. Then, as shown in FIG. 11C, using the normal pixels 93 of the high-sensitive X-ray image 91 and the pixels of the low-sensitive X-ray image 92 at the positions corresponding to the saturated pixels 94, a synthesized X-ray image 95 is generated. That is, the synthesized X-ray image 95 is an image which is formed by replacing the saturated pixels 94 of the high-sensitive X-ray image 91 with the corresponding pixels of the low-sensitive X-ray image 92. In addition, the synthesized X-ray image 95 is generated while the pixel values are adjusted in accordance with the value of the gain at the time of reading each of the high-sensitive X-ray image 91 and the low-sensitive X-ray image 92.

Here, for the sake of simplicity, in the description of the example, the synthesized X-ray image 95 is generated from the two types of the X-ray images of the high-sensitive X-ray image 91 and the low-sensitive X-ray image 92. However, it is same for a case where the synthesized X-ray image is generated from three or more X-ray images with different gains at the time of the reading. That is, using pixels of the high-sensitive image (image with a large gain at the time of the reading) as preferentially as possible, if there are saturated pixels, the synthesized X-ray image is formed by replacing the saturated pixels with the pixel of the X-ray image with the sensitivity subsequently lower than that.

As described above, when the synthesized X-ray image is generated from the X-ray images which are obtained by the multiple reading operations performed with gains varied, it is possible to keep the sensitivity of the synthesized X-ray image as high as possible. Therefore, it is easy to obtain the X-ray image very appropriate for observation of the subject H.

Such processing of synthesizing the high-sensitive image and the low-sensitive image can be performed by using a CMOS type FPD capable of nondestructive reading and by adopting a configuration in which reading is multiply performed with gains varied. Furthermore, in the same order as the first embodiment, determination as to whether or not the rereading is necessary and adjustment of the gain used at the time of rereading are performed. Therefore, in the reread X-ray image, there is no overflow or underflow. Hence, by performing the synthesis processing that replaces the saturated pixels of the high-sensitive image with the pixels of the low-sensitive image, in the synthesized radiographic image, it is possible to perform gradation expression without overflow or underflow in a range from a high-sensitive region to a low-sensitive region.

Incidentally, in the description of the example in the above-mentioned second embodiment, the synthesized X-ray image is generated from the plurality of X-ray images with the different gains at the time of the reading, and is subjected to the offset processing and the defect correction processing. However, after the plurality of X-ray images read from the frame memory 81 is subjected to the offset processing and the defect correction processing, the synthesized X-ray image may be generated. After the offset processing is performed and then the synthesized X-ray image is generated, the defect correction processing may be performed. Alternatively, after the defect correction processing is performed and then the synthesized X-ray image is generated, the offset processing may be performed. Further, the order of the offset processing and the defect correction processing is arbitrary.

In addition, in the description of the example in the above-mentioned first embodiment and second embodiment, when the evaluation value calculation section 76 calculates the evaluation value, the rereading determination section 66 acquires the pixel values of the all the pixels of the captured X-ray image. However, the acquired pixel values do not necessarily have to precisely acquire the pixel values of all the pixels. Specifically, the pixel values are entirely acquired from the entire region of the X-ray image to the extent that the above-mentioned histogram analysis can be performed. The extent that the above-mentioned histogram analysis can be performed is an extent that the resolution and the X-ray image finally used in observation are not extremely different. Consequently, the X-ray image, which is acquired by binning and reading several pixels or performing thinning-out reading, can be used in the calculation of the evaluation value. Further, such an image as can be subjected to the histogram analysis may be used in generation of the synthesized X-ray image.

In the above-mentioned first embodiment and second embodiment, at the first reading, the gain of the amplifier 72 is the initial value $\gamma_0$ determined by the imaging conditions, and thereafter at the time of the rereading, in accordance with the value of the evaluation value M calculated by the evaluation value calculation section 76, the gain may be set to be greater than the initial value $\gamma_0$, or may be set to be less than the initial value $\gamma_0$. However, it is desirable that the gain $\gamma_0$ at the time of the first reading be maximized and the gain be gradually decreased at the rereading thereafter. The reason is that, in the state where there is no irradiation of X-rays, the noise components increase due to the dark current with the elapse of time, and thus the noise components gradually increase. Further, when performing the rereading while gradually decreasing the gain in such a manner, it is desirable to set the gain $\gamma_0$ at the time of the first reading to the maximum in the range appropriate for the imaging conditions.

Further, in the description of the example in the above-mentioned first embodiment and second embodiment, the value of the gain of the amplifier 72, which is reset at the rereading, is calculated as an arbitrary value regardless of the initial value $\gamma_0$. However, it is desirable that the value of the new gain, which is calculated by the gain adjustment section 77, be equal to $(1/2)^n$ (n is an integer other than 0) times the initial value $\gamma_0$. The reason is that the replacement of the reread pixels or the calculation of the pixel values for generation of the synthesized X-ray image can be easily and promptly performed through bit shift.

In addition, in the description of the example in the above-mentioned first embodiment and second embodiment, the rereading is performed while changing the gain of the amplifier 72 of the output circuit 71. However, by making the gain of the transistor M1 of each pixel PX variable, the gain may be adjusted at the step of outputting the voltage signal from each pixel PX. The pixel size of the pixel PX of the FPD 13 is larger than that of a small-size solid-state imaging apparatus used in a digital camera. Hence, a variable gain amplifier can be used in each pixel PX of the FPD 13.

Third Embodiment

Figure 12:
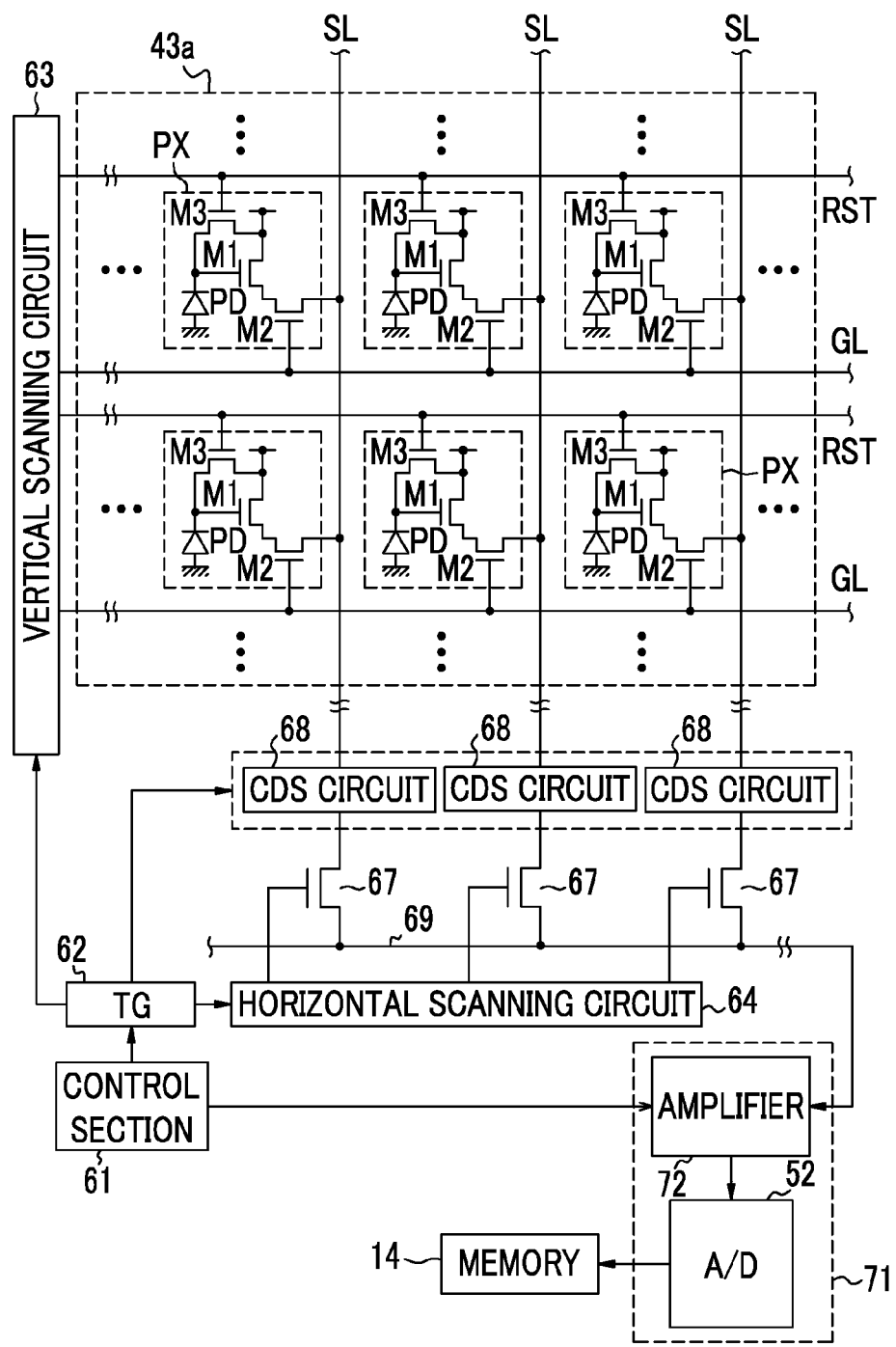
FIG. 12 is an explanatory diagram illustrating a configuration of an FPD.

As shown in FIG. 12, each pixel PX of the FPD 13 is formed of a photodiode PD and transistors M1 to M3, and performs an accumulation operation, a reading operation, and a reset operation, in accordance with driving states of the respective transistors M1 to M3. The accumulation operation is an operation that accumulates the signal electric charge which is generated by photoelectric conversion, and the reading operation is an operation that outputs a voltage signal corresponding to the amount of the accumulated signal electric charge. The reset operation is an operation that drains the accumulated signal electric charge.

The photodiode PD is an element that generates a signal electric charge corresponding to the amount of light incident from the scintillator 41 through photoelectric conversion, and is connected to a gate electrode of an amplification transistor M1 and a source electrode of a reset transistor M3.

In the case where the signal electric charge is accumulated and the case where the voltage signal is read from the pixel PX, the reset transistor M3 is turned off, and a voltage corresponding to the amount of the signal electric charge accumulated in the photodiode PD is applied to the gate electrode of the amplification transistor M1.

A power supply voltage is applied to a source electrode of the amplification transistor M1, and a pixel selection transistor M2 is connected to a drain electrode thereof. Thereby, a voltage corresponding to the amount of the signal electric charge applied to the gate electrode thereof is amplified with a predetermined amplification ratio, and is applied to a source electrode of the pixel selection transistor M2. A gate electrode of the pixel selection transistor M2 is connected to a row selection line GL, and a drain electrode thereof is connected to a signal line SL. Thereby, when a gate signal is input from the row selection line GL, a voltage of the source electrode thereof is output to the signal line SL. Thereby, a voltage signal of the pixel PX is read through the signal line SL. In addition, the FPD 13 is a CMOS type capable of nondestructive reading. Hence, even when the voltage signal is read from the pixel PX, each pixel PX retains the signal electric charge until the reset is performed.

When the signal electric charge accumulated in the photodiode PD is drained, the reset transistor M3 is turned on. A gate electrode of the reset transistor M3 is connected to a reset line RST, and a reset signal is input through the reset line RST. When the reset transistor M3 is turned on in response to the input of the reset signal, the pixel PX at the row drains the signal electric charge accumulated in the photodiode PD into the drain electrode side of the reset transistor M3.

Further, the FPD 13 includes the control section 61, the timing generator (TG) 62, the vertical scanning circuit 63, the horizontal scanning circuit 64, and the like.

The control section 61 integrally controls the respective sections of the FPD 13. The TG 62 generates a timing signal based on an instruction issued from the control section 61. Further, the control section 61 sets the gain of the amplifier 72 of the output circuit 71 to be described later to a value which is obtained through the instruction issued from the console 22, at the time of the reading operation. The vertical scanning circuit 63 and the horizontal scanning circuit 64 are operated based on a clock signal which is input from the TG 62.

The vertical scanning circuit 63 is a driving circuit for the pixels PX, and causes the pixels PX to perform an accumulation operation, a reading operation, or a reset operation by selecting a row of the driven pixels PX and inputting the gate signal and the reset signal to the reset line RST or the row selection line GL of the selected row. The horizontal scanning circuit 64 is a circuit that selects a column of the pixels PX on which the reading of the voltage signal is performed, and selects a column on which the reading is performed by turning on one of column selection transistors 67 provided on the respective signal lines SL.

The row selection line GL is a line for inputting the gate signal, which controls operations of the pixels PX, from the vertical scanning circuit 63, and is provided for each row of the pixels PX. Based on the gate signal which is input through the row selection line GL, the pixel PX performs the accumulation operation or the reading operation. The reset line RST is a line for inputting the reset signal to the pixels PX, and is provided for each row of the pixels PX. The pixels PX in the reset line RST, to which the reset signal is input, are reset by draining the signal electric charges.

The signal line SL is a line for reading the voltage signal (imaging signal) corresponding to the amount of the signal electric charge from each pixel PX, and is provided for each column of the pixels PX. Further, the end of the signal line SL is connected to a correlation double sampling (CDS) circuit 68 and a column selection transistor 67. The CDS circuit 68 operates based on the clock signal which is input from the TG 62, and samples and retains the voltage signals so as to remove noise, which is caused at the reading, from the pixels PX in the row selection line GL which is selected by the vertical scanning circuit 63. The voltage signals, which are retained by the CDS circuit 68, are input to an output circuit 71 through an output bus line 69 by turning on the column selection transistors 67 through the horizontal scanning circuit 64.

The output circuit 71 includes an amplifier 72 and the A/D conversion circuit 52. The amplifier 72 amplifies the voltage signals which are input from the CDS circuit 68, and inputs the signals to the A/D conversion circuit 52. The A/D conversion circuit 52 converts the voltage signals, which are amplified by the amplifier 72, into digital data. The digital data, which is output from the A/D conversion circuit 52, is temporarily stored as an X-ray image in the memory 14, and is transmitted to the console 22 through the communication section 16. The amplifier 72 is a variable gain amplifier capable of freely adjusting the gain. In the reading operation, the gain is set to a predetermined value (initial value $\gamma_1$) based on the imaging conditions at the first reading of the X-ray image, and is set to a new value by the control section 61 in a case of rereading the X-ray image. Further, data, which is output from the output circuit 71, is stored in the memory 14 as described above, and is transmitted to the console 22 through the communication section 16.

Figure 13:
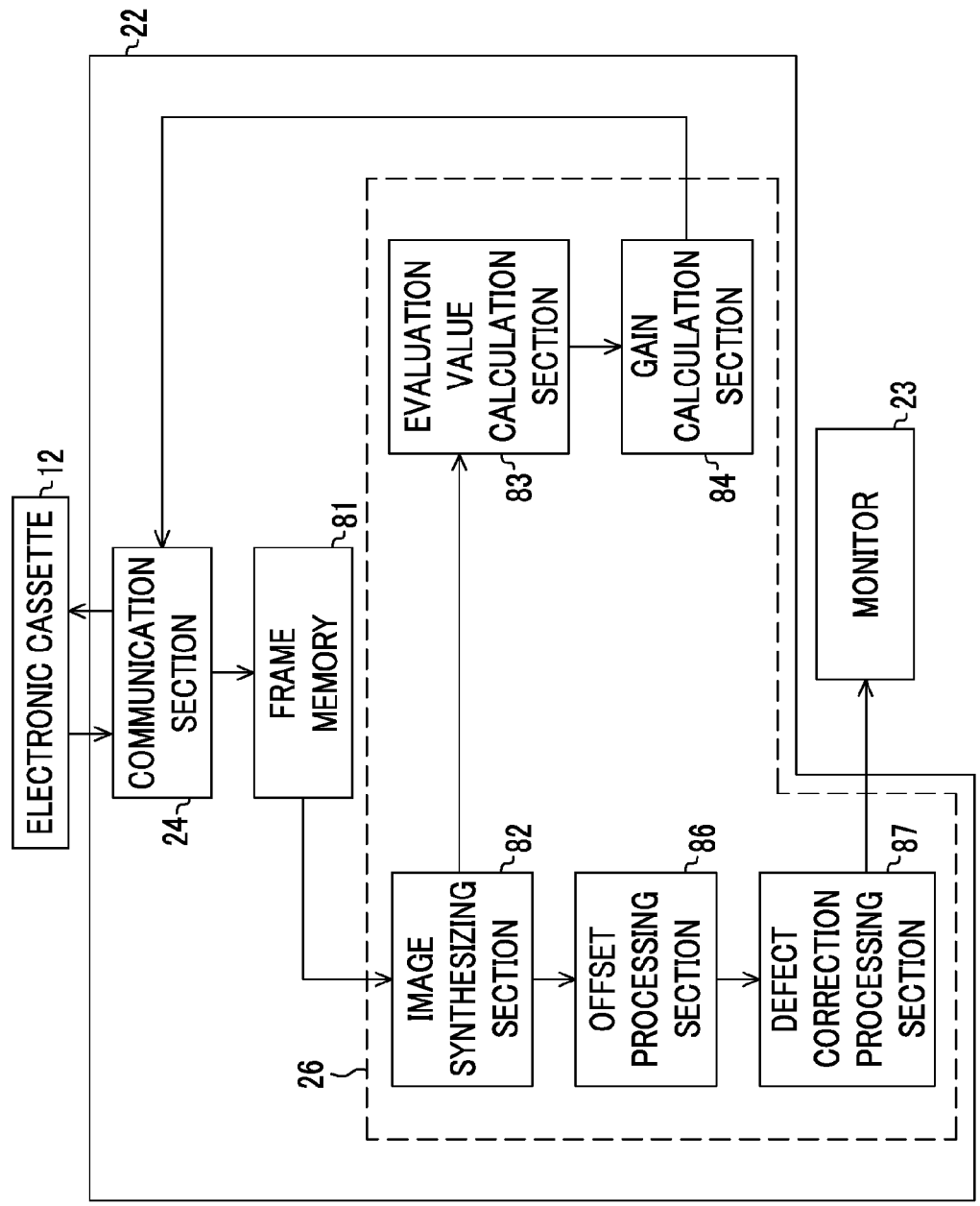
FIG. 13 is a block diagram illustrating a configuration of a console.

As shown in FIG. 13, the console 22 includes the communication section 24, the image processing section 26, and the frame memory 81 described above. The frame memory 81 is a storage device capable of temporarily storing a plurality of X-ray images, and sequentially stores the plurality of X-ray images which are read with the gains of the amplifier 72 varied, as described later.

Further, the image processing section 26 includes an image synthesizing section 82, an evaluation value calculation section 83, a gain calculation section 84, an offset processing section 86, a defect correction processing section 87, and the like.

The image synthesizing section 82 acquires all the plurality of X-ray images which are sequentially stored in the frame memory 81, and generates the synthesized X-ray image in which the X-ray images are synthesized. The synthesized X-ray image is an image which is formed by weighting the plurality of X-ray images acquired from the frame memory 81 in accordance with the gains at the time of reading the respective X-ray images and averaging the images. For example, the synthesized X-ray image $X_c$ is calculated based on $X_c = \Sigma_i (X_i/\gamma_i)/k$ by using the X-ray images $X_i$ (i=1 to k) which are read with the gains of the amplifier 72 as $\gamma_i$ or by multiplying $X_c$ by a predetermined integer. A dynamic range of the synthesized X-ray image becomes larger than that of the original X-ray image. It should be noted that, here, the synthesized X-ray image is generated by weighting the images in accordance with the gains and averaging the images, but the synthesized X-ray image may be generated by simply averaging the X-ray images.

The synthesized X-ray image, which is generated by the image synthesizing section 82 in such a manner, is input to the evaluation value calculation section 83. In addition, at the time of the first reading of the X-ray image, the frame memory 81 stores only a single X-ray image. Hence, when there is only a single X-ray image in the frame memory 81, the image synthesizing section 82 inputs the X-ray image, which is acquired from the frame memory 81, as the synthesized X-ray image to the evaluation value calculation section 83 without performing the image synthesis processing in practice.

The evaluation value calculation section 83 acquires the pixel values of the all the pixels of the synthesized X-ray image from the image synthesizing section 82, calculates the evaluation value, and determines whether or not the rereading is necessary. The calculation of the evaluation value is based on the histogram analysis of the synthesized X-ray image as described below.

As shown in FIG. 6, first, the evaluation value calculation section 83 finds a distribution of the pixel values of all the pixels. The aspect of the distribution of the pixel values has a substantially regular distribution shape in accordance with an imaging target portion (head, chest, abdomen, etc.) without depending on the gain of the amplifier 72. FIG. 6 shows, as an example, a frequency distribution of the pixel values in the case of the X-ray image of the chest of an adult. The distribution A with two peaks indicates a region of the chest tissue (lungs, heart, ribs, etc.), and the distribution B indicates pixels (so-called bypassed pixels) through which the most of the X-rays directly reach the detection surface 43a without being transmitted through the subject H.

The evaluation value calculation section 83 extracts pixels belonging to an effective range E, which is a predetermined region, from the frequency distribution of the pixel values. The effective range E, which is a predetermined region, is determined in advance relative to the distribution shape of the pixel values corresponding to the imaging target portion. Specifically, the range is determined in advance in the frequency distribution so as to include pixels indicating some tissues as main observation targets. For example, in a case of chest X-ray imaging, lungs and the like are main observation targets, and the effective range E is determined in advance relative to the frequency distribution of the pixel values so as to include pixels indicating portions such as lungs and so as not to include other unnecessary pixels such as bypassed pixels of the distribution B.

Incidentally, for the X-ray images before synthesis, the distribution shape itself is substantially invariable in accordance with the imaging target portion. However, when the gain of the amplifier 72 is small, the frequency distribution of the pixel values as shown in FIG. 6 is shifted as a whole to the left side. On the contrary, when the gain of the amplifier 72 is large, the distribution is shifted as a whole to the right side. Thus, comparing the X-ray images having the different gains at the time of the reading with each other, the values of the maximum value $E_2$ and the minimum value $E_1$ of the effective range E are different. However, as described above, the synthesized X-ray image is generated without depending on the values of the gains at the time of reading the respective original X-ray images. Therefore, for the synthesized X-ray image, the distribution shape of FIG. 6 is also maintained, and thus it is possible to extract the pixels which belong to the effective range E and indicate main observation targets.

The evaluation value calculation section 83 calculates an average value of the pixel values of the pixels belonging to the extracted effective range E, and sets the average value as the evaluation value M which is used to determine whether or not the rereading is necessary. Then, as shown in FIG. 7, based on whether or not the evaluation value M is in the appropriate range, it is determined whether or not the rereading is necessary. Specifically, in FIG. 7, as in an evaluation value M2, if the evaluation value M is equal to or greater than the small threshold value $\mu_1$ and equal to or less than the large threshold value $\mu_2$ ($\mu_1 < M < \mu_2$), it is determined that the rereading is not necessary (OK). In contrast, as in an evaluation value M1, if the evaluation value M is smaller than the small threshold value $\mu_1$ ($\mu_1 > M$), or, as in an evaluation value M3, if the evaluation value M is greater than the large threshold value $\mu_2$ ($M > \mu_2$), it is determined that the rereading is necessary (NG). The reason is as follows. If the evaluation value M is less than the small threshold value $\mu_1$, the gain of the amplifier 72 is excessively small, and thus underflow occurs. If the evaluation value M is greater than the large threshold value $\mu_2$, the gain of the amplifier 72 is excessively large, and thus overflow occurs. As a result, the read X-ray image is inappropriate for observation of the subject H. Specific values of the small and large threshold values $\mu_1$ and $\mu_2$ relative to the evaluation value M are determined such that no overflow or underflow occurs in the subject H (at least the main observation targets in the subject H).

If it is determined that it is necessary to reread the X-ray image, the evaluation value calculation section 83 inputs the calculated evaluation value M to the gain calculation section 84.

If it is determined that the rereading is necessary (NG) by the evaluation value calculation section 83, the gain calculation section 84 calculates a value of the gain of the amplifier 72 at the time of the rereading based on the evaluation value M which is input from the evaluation value calculation section 83.

Specifically, at the time of determining whether or not the rereading is necessary in the evaluation value calculation section 83, if the evaluation value M is less than the small threshold value $\mu_1$ ($\mu_1 > M$), the gain calculation section 84 calculates a value $\gamma_2$ ($\gamma_1 < \gamma_2$) greater than the initial value $\gamma_1$ in accordance with the value of the evaluation value M. In contrast, if the threshold value M is greater than the large threshold value $\mu_2$ ($M > \mu_2$), the gain calculation section 84 calculates a value $\gamma_2$ ($\gamma_1 < \gamma_2$) less than the initial value $\gamma_1$ in accordance with the value of the evaluation value M. The initial value $\gamma_1$ of the gain of the amplifier 72 is determined by the imaging conditions as described above.

The value of the new gain calculated by the gain calculation section 84 is transmitted to the electronic cassette 12 through the communication section 24, together with the rereading instruction. When the control section 61 receives the rereading instruction, the electronic cassette 12 sets the gain of the amplifier 72 to the value of the new gain calculated by the gain calculation section 84, and performs the reading operation again. The X-ray image, which is read with the new gain, is transmitted to the console 22, is stored in the frame memory 81, is read by the image synthesizing section 26, and is used in the generation of the synthesized X-ray image.

In addition, if the evaluation value calculation section 83 determines that the rereading is not necessary (OK), the image synthesizing section 82 inputs the generated synthesized X-ray image to the offset processing section 86. The offset processing section 86 performs the offset processing on the input synthesized X-ray image, and inputs the image to the defect correction processing section 87. The defect correction processing section 87 performs the defect correction processing on the synthesized X-ray image after the offset processing.

Further, if the evaluation value calculation section 83 determines that the rereading is not necessary (OK), the evaluation value calculation section 83 transmits the control signal, which indicates that the rereading is not necessary, to the electronic cassette 12 through the communication section 24, instead of inputting the evaluation value M to the gain calculation section 84. When receiving the control signal which indicates that the rereading is not necessary from the console 22, the electronic cassette 12 performs the reset operation, and drains the signal electric charges accumulated in the pixels PX.

Hereinafter, an effect of the X-ray imaging system 10 configured as described above will be described with reference to the flowchart shown in FIG. 14.

Figure 14:
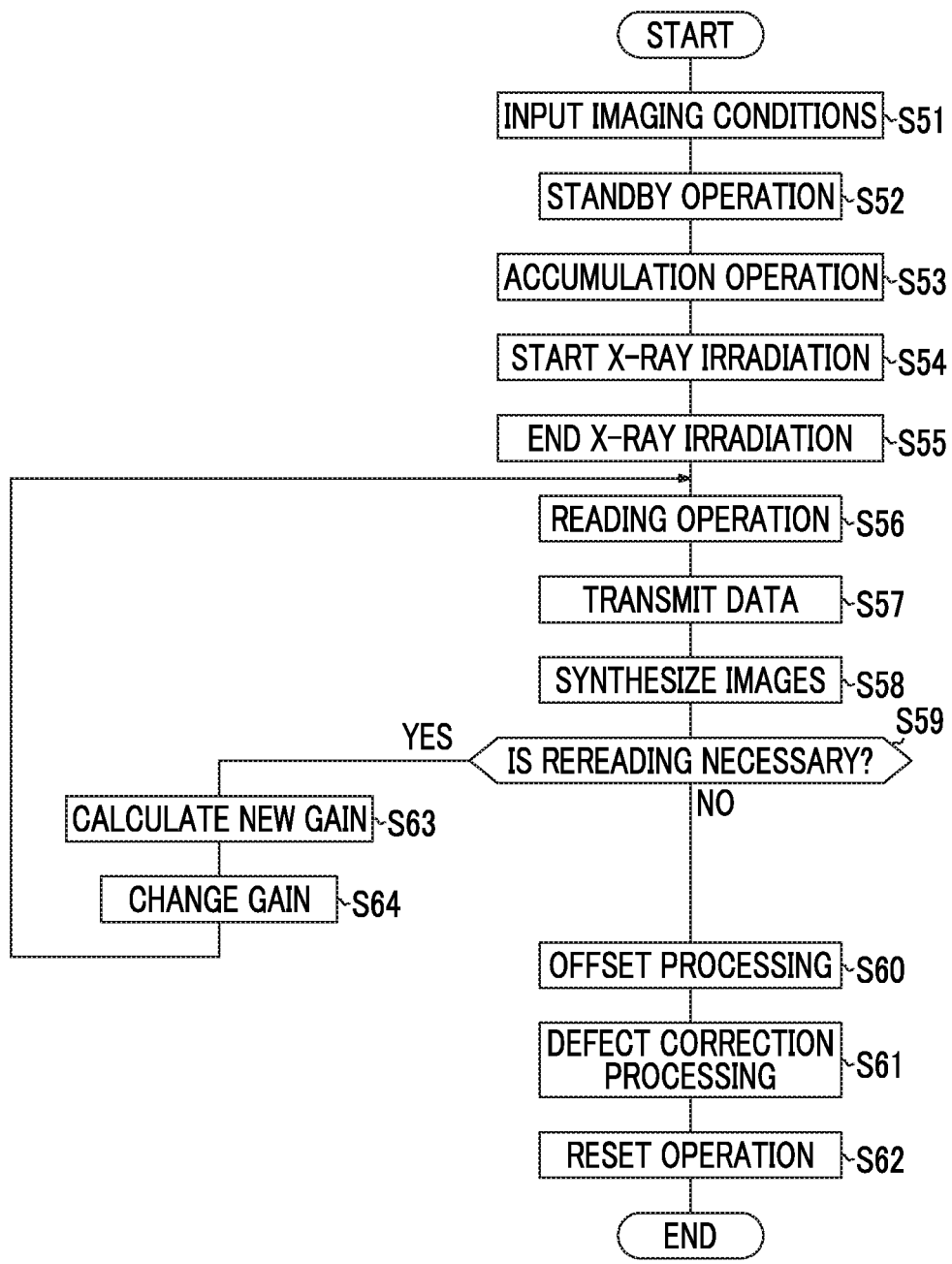
FIG. 14 is a flowchart illustrating an effect of the X-ray imaging system.

As shown in FIG. 14, when the X-ray imaging system 10 performs the X-ray imaging, first, the imaging conditions are input to the radiation source controller 19 and the console 22 (step S51). The radiation source controller 19 receives inputs of the tube voltage, the tube current, the irradiation time of the X-ray tube as the imaging conditions. The imaging conditions, which are input to the radiation source controller 19, are determined by the imaging target portion, the physical size and the age of the subject H, and the like which are confirmed by the imaging order received by the console 22.

The imaging conditions, which are input to the console 22, are transmitted to the electronic cassette 12 through the communication section 24. The electronic cassette 12 starts a standby operation when the imaging conditions are input from the console 22 (step S52). The standby operation is an operation that waits for start of irradiation of X-rays by repeating the reset operation at predetermined timing.

When the irradiation switch 21 is pressed, the synchronization start signal is transmitted to the X-ray source 17 through the radiation source controller 19, and the X-ray source 17 is shifted to a ready state. When the X-ray source 17 is in the ready state, the radiation source controller 19 transmits the accumulation start signal to the console 22, and the electronic cassette 12 starts the accumulation operation (step S53).

Further, when the electronic cassette 12 shifts to the accumulation operation, the radiation source control section 19 receives the irradiation start signal from the console 22, and starts irradiation of X-rays by using the tube voltage and the tube current corresponding to the imaging conditions from the X-ray source 17 (step S54).

The radiation source controller 19 monitors the timer. If the irradiation time set by the imaging conditions has elapsed, the controller sends an end synchronization signal to the X-ray source 17, and ends the irradiation of X-rays (step S55). At the same time, the radiation source controller 19 transmits the end synchronization signal to the console 22, and the console 22 shifts the electronic cassette 12 from the accumulation operation to the reading operation (step S56). At the first reading (first time) in the reading operation, the gain of the amplifier 72 of the output circuit 71 is set to a predetermined value (initial value) $\gamma_1$ corresponding to the imaging conditions, and all pixels are nondestructively read in that state.

When the gain of the amplifier 72 is set to the initial value $\gamma_1$ and the first reading is completed, the X-ray image, which is obtained by the first reading, is converted into digital data by the A/D converter 52 and is temporarily stored in the memory 14. The data of the X-ray image, which is stored in the memory 14, is transmitted to the console 22 through the communication sections 16 and 24, and is stored in the frame memory 81 (step S57).

The X-ray image, which is stored in the frame memory 81, is read by the image synthesizing section 82, thereby the synthesized X-ray image is generated (step S58), and is input to the evaluation value calculation section 83, and it is determined whether or not the rereading is necessary (step S59). In addition, here, since the reading is first reading, practically the image synthesizing section 82 does not perform the synthesis processing, and determines whether or not the rereading is necessary, based on the X-ray image which is input as the synthesized X-ray image, when the X-ray image acquired from the frame memory 81 is input as the synthesized X-ray image to the evaluation value calculation section 83. As described later, when a plurality of X-ray images is stored in the frame memory 81 through the rereading, the image synthesizing section 82 reads the X-ray images, and inputs an average image thereof as a synthesized X-ray image to the evaluation value calculation section 83. The evaluation value calculation section 83 calculates the evaluation value M by performing the histogram analysis of the X-ray image as shown in FIG. 6. Then, as shown in FIG. 7, comparing the evaluation value M with predetermined small and large threshold values $\mu_1$ and $\mu_2$, it is determined whether or not the rereading is necessary.

If the evaluation value M is equal to or greater than the small threshold value $\mu_1$ and equal to or less than the large threshold value $\mu_2$ (the evaluation value M2 in FIG. 7), the evaluation value M is in the appropriate range. Therefore, the gain of the amplifier 72 at the time of reading the X-ray image is appropriate, and it is determined that the rereading is not necessary (OK). In this case, the rereading of the X-ray image is not performed, and the image synthesizing section 82 inputs the X-ray image acquired from the frame memory 81 as the synthesized X-ray image to the offset processing section 86, and performs the offset processing (step S60). The synthesized X-ray image after the offset processing is subjected to the defect correction processing by the defect correction processing section 87 (step S61), and is displayed on the monitor 23, or transmitted to the image server (not shown).

Further, if it is determined that the rereading is not necessary (OK), the control signal, which indicates the determination, is input to the electronic cassette 12, the electronic cassette 12 performs the reset operation, and drains the signal electric charges accumulated in the pixels PX.

In contrast, as in a case where the evaluation value M is less than the small threshold value $\mu_1$ (in the case of the evaluation value M1 in FIG. 7), or as in a case where the evaluation value M is greater than the large threshold value $\mu_2$ (in the case of the evaluation value M3 in FIG. 7), if the evaluation value M is outside of the appropriate range, it is determined that the gain of the amplifier 72 at the time of the first reading of the X-ray image is less than or greater than an appropriate value. As a result, it is determined that the rereading is necessary after the gain is adjusted. In this case, the gain calculation section 84 calculates a new gain based on the evaluation value M which is input from the evaluation value calculation section 83 (step S63), and transmits the new gain together with the rereading instruction to the electronic cassette 12 through the communication section 24.

As in the evaluation value M1, the evaluation value M is less than the small threshold value $\mu_1$. Hence, if it is determined that the rereading is necessary, the new gain, which is calculated by the gain calculation section 84, becomes the value $\gamma_2$ ($\gamma_2 > \gamma_1$) which is larger than the initial value $\gamma_1$. In contrast, as in the evaluation value M3, the evaluation value M is greater than the large threshold value $\mu_2$. Hence, if it is determined that the rereading is necessary, the new gain, which is calculated by the gain calculation section 84, becomes the value $\gamma_2$ ($\gamma_2 < \gamma_1$) less than the initial value $\gamma_1$.

When receiving the rereading instruction and the new gain calculated by the gain calculation section 84, the electronic cassette 12, first, sets the gain of the amplifier 72 to the new value calculated by the gain calculation section 84 (step S64). In such a manner, when the gain of the amplifier 72 is reset, the respective sections are controlled based on the rereading instruction, and the reading operation is performed again (S56).

The X-ray image, which is obtained by performing the rereading with the new gain, is transmitted to the console 22 (S57) as described above, and is additionally stored in the frame memory 81. Hence, at the time point the rereading is performed once, the frame memory 81 stores two X-ray images of: the X-ray image which is obtained first and read with the gain $\gamma_1$ (hereinafter referred to as a first X-ray image in accordance with the reading order); and the X-ray image which is obtained second and reread with the gain $\gamma_2$ (hereinafter referred to as a second X-ray image).

In such a manner, when the X-ray image, which is read with the value of the gain of the amplifier 72 set as $\gamma_2$, is added to the frame memory 81, the image synthesizing section 82 acquires the first X-ray image and the second X-ray image, and synthesizes them, thereby generating a new synthesized X-ray image. The synthesized X-ray image, which is generated from the first X-ray image and the second X-ray image, is input to the evaluation value calculation section 83 again, and it is determined whether or not the rereading is necessary (S19).

Here, if it is determined gain that the rereading is necessary (NG), the above-mentioned rereading is performed again. That is, the cycle (S59→S63→S64→S56→S57→S58) of the rereading is repeated until it is determined that the rereading is not necessary (OK), based on the synthesized X-ray image which is newly generated for each cycle.

If it is determined that the rereading is not necessary (OK), the synthesized X-ray image is subjected to the offset processing (S60) and the defect correction processing (S61), and is displayed on the monitor 23, or transmitted to the image server (not shown), and the electronic cassette 12 performs the reset operation, and drains the signal electric charges accumulated in the pixels PX (S62).

As described above, the X-ray imaging system 10 performs histogram analysis by using all the pixels of the synthesized X-ray image (which is actually the X-ray image at the first reading), and determines whether or not the rereading is necessary, based on the analysis result. If it is determined that the rereading is necessary, the rereading is performed by adjusting the gain of the amplifier 72 of the output circuit 71, and the synthesized X-ray image is generated again. Therefore, in the synthesized X-ray image which is finally used for observation, there is no overflow or underflow, and the image can be appropriately used for the main observation targets of the subject H.

Further, in the X-ray imaging system 10, in the adjustment of the gain used at the time of reading the X-ray image, by not using the pixel values of the determination pixels distributed in the detection surface as in the existing system but using the pixel values of all the pixels within the detection surface, the gain is adjusted. Hence, it is possible to determine an appropriate value of the gain based on the amount of incident X-rays in which the physical size of the subject H, the imaging target portion, or the like is more precisely reflected. Therefore, as compared with the existing system, it is possible to perform more appropriate gain adjustment. At the same time, the synthesized X-ray image, which is formed by averaging the plurality of X-ray images with different values of the gains at the time of the reading, is finally set as the X-ray image for observation. Therefore, even when the value of the gain which is set at the time of the rereading is slightly deviated from an optimum value, the effect is rarely exerted on the X-ray image for observation. Hence, even when the dosing amount is set to be low in the low-dosing amount imaging conditions, the X-ray imaging system 10 is able to obtain the X-ray image with good image quality. Such an effect contributes to reduction in the amount of radiation exposure of the subject H.

Further, when the rereading is performed (when total two or more reading operations are performed), by adjusting the gains at the time of the second and following reading of the X-ray images, it is possible to obtain the X-ray image with better image quality, compared with the case of obtaining the X-ray image and thereafter adjusting the density of the X-ray image through the image processing such as gradation conversion processing. The reason is that, in the case of using the image processing, it is difficult to improve the S/N to the noise caused by the ASIC such as the IC chip 47, but in the X-ray imaging system 10, the signal values are adjusted at the step of reading the signal sent from the FPD 13, and thus the S/N can be improved.

In the description of the analysis using the image histogram of the present example, the following example was given: the evaluation value calculation section 83 extracts pixels belonging to an effective range E, from the frequency distribution of the pixel values of the read X-ray image, and sets the average value of all the pixel values as the evaluation value M. However, the average value between the maximum value $E_2$ and the minimum value $E_1$ of the effective range E may be simply set as the evaluation value M. Alternatively, the evaluation value M may be acquired by using a partial region of the effective range E. For example, when the object of interest is a bone portion, the average value of the pixels corresponding to the bone portion in the effective range E may be set as the evaluation value M, or when the object of interest is a lung, the average value of the pixels corresponding to the lung in the effective range E may be set as the evaluation value M. In addition, the average value of all the pixels, which are not limited to the pixels in the effective range E and also includes the pixels of the bypass region, may be set as the evaluation value M. However, since the effective range E is a region that indicates the imaging target portion of the subject H, as described in the above example, it is desirable to use the pixel values belonging to the effective range E.

Further, the effective range E is changed by the gain of the amplifier 72. Specifically, when the gain is less than the appropriate value, the frequency distribution of the pixel values shown in FIG. 6 is shifted to the left side (negative side). In contrast, when the gain is greater than the appropriate value, the frequency distribution of the pixel values is shifted to the right side (positive side). Furthermore, the width of the frequency distribution is changed depending on the magnitude of the gain. Accordingly, by determining the width of the effective range E in advance in the case where the gain is the appropriate value and acquiring an amount of deviation between the width thereof and a width of the effective range E of the actually read X-ray image as the evaluation value M, the determination as to whether or not the rereading is necessary and the calculation of the new gain may be performed.

Figure 15:
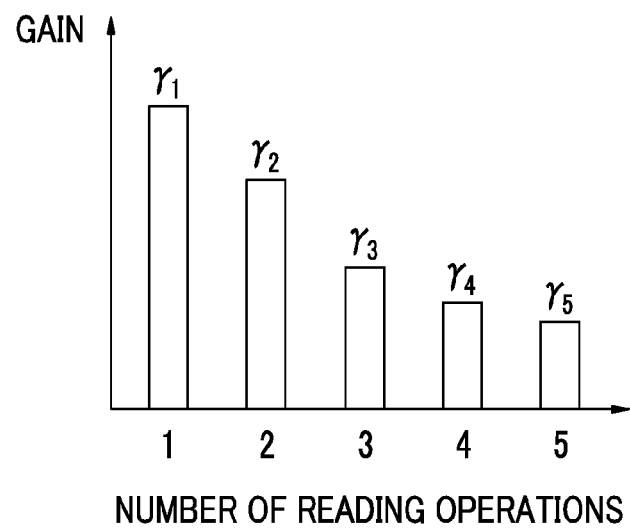
FIG. 15 is a diagram illustrating a magnitude relationship of gains.

In addition, in the description of the example in the above-mentioned third embodiment, the value of the gain, which is set at the time of the rereading, may become greater than or may become less than the gain $\gamma_1$ at the time of the first reading. However, whenever the rereading is performed, it is desirable that the rereading be performed with a gain less than the previous gain. For example, as shown in FIG. 15, when total five reading operations are performed on the X-ray image, the gain $\gamma_2$, which is set at the time of the second reading, is a value in a range less than the gain $\gamma_1$ at the time of the first reading (first time). Further, the gain $\gamma_3$, which is set at the time of the third reading, is a value in a range less than the gain $\gamma_2$ at the time of the second reading. It is the same for the fourth and following reading operations, and thus $\gamma_1 > \gamma_2 > \gamma_3 > \gamma_4 > \gamma_5 > \ldots$. As described above, the rereading is performed while the gain used at the time of rereading is gradually decreased. The reason is that, even in a state where there is no irradiation of X-rays, the noise components increase due to the dark current with the elapse of time, and thus the noise components become large if the high-sensitive (high-gain) reading is performed later. In such a manner, when the gain is gradually decreased for each rereading, the gain $\gamma_1$ at the time of the first reading (first time) is a value which determined in advance based on the imaging conditions as described above. However, the gain $\gamma_1$ at the time of the first reading is intentionally set to be higher than the appropriate value. In this way, based on the evaluation value M calculated by the evaluation value calculation section 83, the above-mentioned conditions are also easily satisfied.

Figure 16:
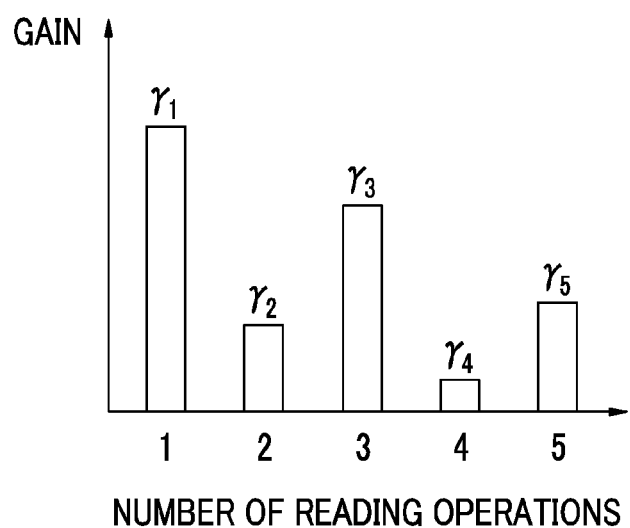
FIG. 16 is a diagram illustrating another example of the magnitude relationship of gains.

Further, it is desirable that, when the rereading is performed, the values of the gains alternately increase/decrease, like a large gain, a small gain, a large gain, a small gain, . . . . Specifically, as shown in FIG. 16, the second gain $\gamma_2$ is set to a value less than the first gain $\gamma_1$ ($\gamma_2 < \gamma_1$). In contrast, the third gain $\gamma_3$ is set to be greater than the second gain $\gamma_2$ ($\gamma_3 > \gamma_2$). Furthermore, the fourth gain $\gamma_4$ is set to be less than the third gain $\gamma_3$ ($\gamma_4 < \gamma_3$). It is the same for the following gains. As described above, when the values of the gains of the amplifier 72 at the time of the reading alternately increase/decrease, in the determination as to whether or not the rereading is necessary, it is possible to shorten the time until it is determined that the rereading is not necessary (OK). That is, it is possible to more promptly obtain the X-ray image (synthesized X-ray image) very appropriate for observation.

Furthermore, it is desirable that the gains $\gamma_1$, $\gamma_3$, $\gamma_5$, . . . which are set with high gains at the time of the odd-number-th reading sequentially decrease with an increase in the number of times the reading is performed ($\gamma_1 > \gamma_3 > \gamma_5 > \ldots$). Likewise, it is desirable that the gains $\gamma_2$, $\gamma_4$, $\gamma_6$, . . . which are set with low gains at the time of the even-number-th reading sequentially decrease with an increase in the number of times the reading is performed ($\gamma_2 > \gamma_4 > \gamma_6 > \ldots$). In this way, while reducing the noise caused by the dark current as described above, it is also possible to more promptly obtain the X-ray image (synthesized X-ray image) very appropriate for observation. It is apparent that even just either $\gamma_1 > \gamma_3 > \gamma_5 > \ldots$ or $\gamma_2 > \gamma_4 > \gamma_6 > \ldots$ may be satisfied. In this case, compared with a case where such a condition is not satisfied, while reducing the noise caused by the dark current as described above, it is also possible to more promptly obtain the X-ray image (synthesized X-ray image) very appropriate for observation.

Fourth Embodiment

Incidentally, in the above-mentioned third embodiment, when the X-ray image is reread, it is determined whether or not the rereading is necessary. Hence, it is not determined how many times the rereading is performed finally. However, as described later, when the rereading is performed, the number of times the rereading is performed may be determined.

For example, the evaluation value calculation section 82 performs the histogram analysis on the synthesized X-ray image (which is the X-ray image obtained through the first reading), which is obtained first from the image synthesizing section 82, as described above, and thereby determines whether or not the rereading is necessary. If it is determined that the rereading is necessary (NG), by evaluating the granularity of the synthesized X-ray image, a second evaluation value, which indicates the granularity of the synthesized X-ray image, is calculated. The granularity is an indicator for evaluating the S/N of an image, where the larger the second evaluation value, the larger the number of noise components, and the smaller the second evaluation value, the smaller the number of noise components. The evaluation of the granularity of the synthesized X-ray image may be performed on the entirety of the synthesized X-ray image, and the granularity of only the site of interest may be evaluated.

Further, the number of the rereading operations, which is optimum depending on the second evaluation value, is determined in advance through experiment, and a look-up table (LUT), in which the second evaluation value is associated with the number of the rereading operations, is stored in a memory which is not shown. Then, the evaluation value calculation section 82 calculates the optimum number of the rereading operations n (n is an integer not less than 1) by comparing the calculated second evaluation value Q with the LUT.

Further, the gain calculation section 84 receives inputs of the first evaluation value M, which is obtained by the histogram analysis from the evaluation value calculation section 82, and the optimum number n of the rereading operations which is calculated based on the granularity of the synthesized X-ray image. Then, based on the first evaluation value M and the number n of the rereading operations, the gains of the amplifier 72 at the time of the respective rereading operations are calculated. For example, when the rereading is performed four times (n=4), all the gains $\gamma_2$, $\gamma_3$, $\gamma_4$, and $\gamma_5$ at the time of the second to fifth reading operations are calculated from the gain $\gamma_1$ at the time of the first reading and the first evaluation value M.

Figure 17:
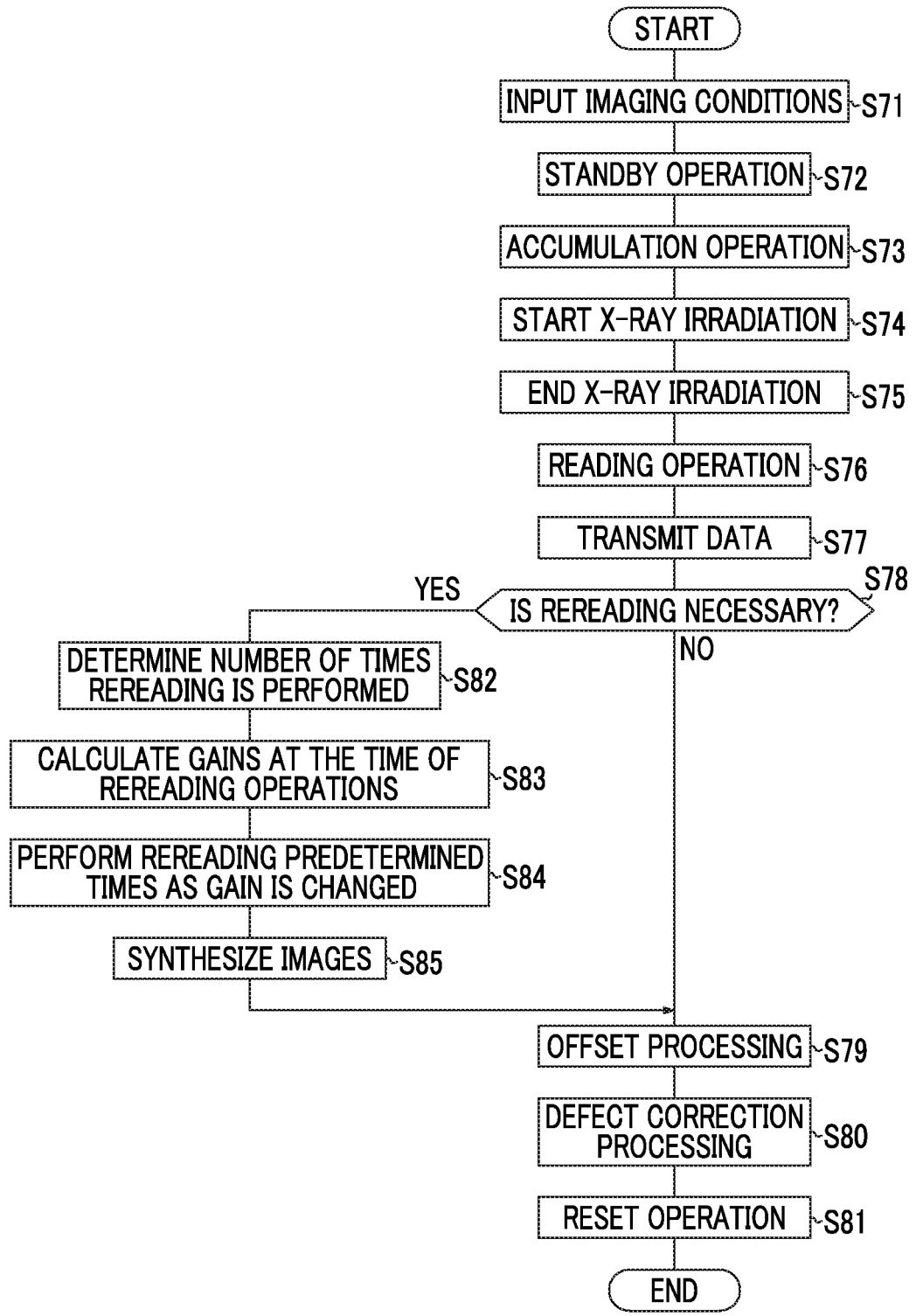
FIG. 17 is a flowchart illustrating an aspect in which the number of rereading operations is set in advance.

In the case of the above-mentioned fourth embodiment, the X-ray imaging system 10 operates as follows. As shown in FIG. 17, the process (steps S71 to S77), which is performed until the first X-ray image is transmitted from the input of the imaging conditions to the console 22 and is stored in the frame memory 81, is the same as that of steps S11 to S17 of the third embodiment mentioned above.

When the read X-ray image is transmitted first to the console 22, the image synthesizing section 82 acquires the first X-ray image which is stored in the frame memory 81, and inputs the image as the synthesized X-ray image to the evaluation value calculation section 83. Then, the evaluation value calculation section 83 calculates the first evaluation value M from the input synthesized X-ray image, and determines whether or not the rereading is necessary based on the calculated evaluation value M (step S78). Here, the method of determining whether or not the rereading is necessary is the same as the above-mentioned third embodiment.

As a result of the determination, if it is determined that the rereading is not necessary, the synthesized X-ray image is subjected to the offset processing (step S79) and the defect correction processing (step S80), and is set as the X-ray image for observation. Further, when the X-ray image for observation is obtained, the electronic cassette 12 performs the reset operation, and drains the signal electric charges accumulated in the pixels PX.

In contrast, if it is determined that the rereading is necessary, the evaluation value calculation section 83 further evaluates the granularity of the synthesized X-ray image, and calculates a second evaluation value Q. Then, by comparing the predetermined LUT with the calculated second evaluation value, the optimum number n of the rereading operations is determined (step S82).

When the optimum number n of the rereading operations is determined, based on the first evaluation value M and the optimum number n of the rereading operations, the gain calculation section 84 newly calculates each of the gains of the amplifier 72 at the respective rereading operations (step S83).

While the new gains of the amplifier 72 at the respective rereading operations are set based on the optimum number n of the rereading operations calculated in such a manner, n rereading operations are performed (step S84). At this time, the X-ray images, which are obtained through the n rereading operations, are stored in the memory 14 in the read order, and sequentially transmitted to the console 22.

When the n rereading operations are completed and the X-ray image obtained through the first reading and the n X-ray images obtained through the n rereading operations are stored in the frame memory 81, the image synthesizing section 82 acquires all the X-ray images from the frame memory 81, and generates the synthesized X-ray image by using those (S85). The synthesized X-ray image, which is generated in such a manner, is subjected to the offset processing (S79) and the defect correction processing (S80), and is displayed as the X-ray image for observation on the monitor 23, or transmitted to the image server (not shown). Further, when the X-ray image for observation is obtained in such a manner, the electronic cassette 12 performs the reset operation, and drains the signal electric charges accumulated in the pixels PX.

As in the above-mentioned third embodiment, whenever the rereading is repeatedly performed in a state where the number of times the rereading is performed is not determined, it is determined whether or not the rereading is necessary, and the gain at the time of the next reading is calculated. Then, even when the gains at the time of the respective rereading operations are optimum, there may be an increase in the number of rereading operations which are performed until the X-ray image for observation (synthesized X-ray image) is finally obtained. As the number of rereading operations increases, the time necessary to obtain the X-ray image for observation increases. However, as described above, the granularity of the X-ray image (synthesized X-ray image) obtained through the first reading is evaluated, the number of rereading operations n is determined based on the evaluation. Further, based on the number of rereading operations n together with the first evaluation value M, the optimum gain at the time of rereading is calculated by the imaging conditions, and the n rereading operations are performed. With such a configuration, compared with the aspect of the above-mentioned third embodiment, it is possible to reduce the number of the rereading operations and more promptly obtain the X-ray image for observation.

Fifth Embodiment

Further, in the example of the above-mentioned fourth embodiment, the determination as to whether or not the rereading is necessary and the calculation of the number n of the rereading operations based on the granularity evaluation are performed based on the X-ray image which is read first in practice, but may be performed as follows. For example, as shown in FIG. 18, if it is determined that the rereading is necessary (S98), the granularity is not evaluated based on the first X-ray image (synthesized X-ray image), and the rereading (the second reading in the whole process) is performed in a similar manner to the above-mentioned fourth embodiment (step S111). Then, the X-ray image, which is obtained through the second reading, is transmitted to the console 22 (step S112), and the synthesized X-ray image is generated from the X-ray image obtained through the first reading and the X-ray image obtained through the second reading (step S113).

Then, the evaluation value calculation section 83 evaluates the granularity of the synthesized X-ray image which is generated from the first X-ray image and the second X-ray image, compares the LUT with the evaluation value Q, thereby calculating the number n of the rereading operations (step S114). In this case, n is an integer (nonnegative integer) including 0. Subsequently, as in the above-mentioned example, the gain calculation section 84 calculates the gains of the respective rereading operations (step S115), and performs the n rereading operations while adjusting the gain of the amplifier 72 to the calculated value (step S116). The X-ray images, which are obtained through the n rereading operations, are temporarily stored in the memory 14, and sequentially transmitted to the console 22.

In such a manner, the X-ray images, which are obtained through the n+2 reading operations, are synthesized again by the image synthesizing section 82 (S99), are subjected to the offset processing (S100) and the defect correction processing (S101), and are thereafter displayed on the monitor 23, or transmitted as to the image server (not shown). When the X-ray image for observation is obtained in such a manner, the electronic cassette 12 performs the reset operation, and drains the signal electric charges accumulated in the pixels PX (S102).

As described above, when the optimum number n of the rereading operations is determined in advance based on the evaluation of the granularity, by evaluating the granularity of the synthesized X-ray image which is generated from the X-ray image obtained through the first reading and the X-ray image obtained through the second reading, the number n of the rereading operations is determined. Then, based on the X-ray image obtained through the first reading as described above, compared with the case of calculating the number n of the rereading operations, the number of the rereading operations is highly likely to be further optimized.

It should be noted that, in the above-mentioned example, the granularity of the synthesized X-ray image is evaluated in order to calculate the optimum number n of the rereading operations, but things other than the granularity may be evaluated if the amount of noise of the synthesized X-ray image can be evaluated.

It should be noted that, in the description of the example in the above-mentioned embodiment, when the synthesized X-ray image is generated, the original X-ray images are averaged, but the invention is not limited to this. For example, the synthesized X-ray image may be generated in the following manner. As described above, the plurality of X-ray images is stored in the frame memory 81 with respectively different gains. However, for the sake of simplicity, it is assumed that the following two types of the X-ray images are obtained: one is a high-sensitive X-ray image 91 which is read with a high gain as shown in FIG. 11A; and the other is a low-sensitive X-ray image 92 which is read with a low gain as shown in FIG. 11B. In the high-sensitive X-ray image 91, there are pixels (hereinafter referred to as normal pixels) 93 with normal pixel values indicating the subject H and pixels (hereinafter referred to as saturated pixels) 94 of which the pixel values are saturated. The normal pixels 93 are pixels, of which the amounts of the signal electric charges are not saturated and do not reach the upper limit of the output of the amplifier 72, in the pixels PX of the FPD 13 and are pixels substantially indicating the subject H. In contrast, the saturated pixels 94 are pixels, of which the signal electric charges generated in the pixels PX of the FPD 13 are saturated, or pixels of which the signal electric charges reach the upper limit of the output of the amplifier 72 since the gain of the amplifier 72 is high even when the signal electric charges generated in the pixels PX of the FPD 13 are not saturated. Since the signal electric charges generated in the pixels PX of the FPD 13 are saturated, the pixels, which become the saturated pixels 94, are mostly bypassed pixels. However, reaching the upper limit of the output of the amplifier 72 since the gain is excessively high may occur even in the pixels indicating the subject H.

On the other hand, the low-sensitive X-ray image 92 is an image which is read in a state where the gain of the amplifier 72 is set to be low. Hence, in the image, at least the pixels, which indicate abnormal pixel values reaching the upper limit of the output of the amplifier 72 since the gain of the amplifier 72 is excessively high, are reduced. Here, in the low-sensitive X-ray image 92, as the gain at the time of the reading is low, all the pixels including the bypassed pixel indicate normal pixel values, and thus it is assumed that there is no pixel (no underflow) with a pixel value which is too low to contribute to resolution of the image. However, since the gain of the amplifier 72 at the time of the reading is low, the S/N thereof is worse than that of the high-sensitive X-ray image 91.

When the high-sensitive X-ray image 91 and the low-sensitive X-ray image 92 are obtained, the image synthesizing section 82, first, specifies positions of the saturated pixels 94 of the high-sensitive X-ray image 91, and extracts the normal pixels 93 of the high-sensitive X-ray image 91. Thereafter, from the low-sensitive X-ray image 92, the pixels, which are at the same positions as the saturated pixels 94 extracted from the high-sensitive X-ray image 91, are extracted. Then, as shown in FIG. 11C, using the normal pixels 93 of the high-sensitive X-ray image 91 and the pixels of the low-sensitive X-ray image 92 at the positions corresponding to the saturated pixels 94, a synthesized X-ray image 95 is generated. That is, the synthesized X-ray image 95 is an image which is formed by replacing the saturated pixels 94 of the high-sensitive X-ray image 91 with the corresponding pixels of the low-sensitive X-ray image 92. In addition, the synthesized X-ray image 95 is generated while the pixel values are adjusted in accordance with the value of the gain at the time of reading each of the high-sensitive X-ray image 91 and the low-sensitive X-ray image 92.

Here, for the sake of simplicity, in the description of the example, the synthesized X-ray image 95 is generated from the two types of the X-ray images of the high-sensitive X-ray image 91 and the low-sensitive X-ray image 92. However, it is same for a case where the synthesized X-ray image is generated from three or more X-ray images with different gains at the time of the reading. That is, using pixels of the high-sensitive image (image with a large gain at the time of the reading) as preferentially as possible, if there are saturated pixels, the synthesized X-ray image is formed by replacing the saturated pixels with the pixel of the X-ray image with the sensitivity subsequently lower than that.

As described above, when the synthesized X-ray image is generated from the X-ray images which are obtained by the multiple reading operations performed with gains varied, it is possible to keep the sensitivity of the synthesized X-ray image as high as possible. Therefore, it is easy to obtain the X-ray image very appropriate for observation of the subject H.

Incidentally, in the above-mentioned embodiment, the synthesized X-ray image is generated from the plurality of X-ray images with the different gains at the time of the reading, and is subjected to the offset processing and the defect correction processing. However, after the plurality of X-ray images read from the frame memory 81 is subjected to the offset processing and the defect correction processing, the synthesized X-ray image may be generated. After the offset processing is performed and then the synthesized X-ray image is generated, the defect correction processing may be performed. Alternatively, after the defect correction processing is performed and then the synthesized X-ray image is generated, the offset processing may be performed. Further, the order of the offset processing and the defect correction processing is arbitrary.

In addition, in the description of the example in the above-mentioned first embodiment and second embodiment, the value of the gain of the amplifier 72, which is reset at the rereading, is calculated as an arbitrary value regardless of the initial value $\gamma_1$. However, it is desirable that the value of the new gain, which is calculated by the gain calculation section 84, be equal to $(\frac{1}{2})^n$ (n is an integer other than 0) times the initial value $\gamma_1$. The reason is that the replacement of the reread pixels or the calculation of the pixel values for generation of the synthesized X-ray image can be easily and promptly performed through bit shift.

In addition, in the description of the example in the above-mentioned embodiment, the rereading is performed while changing the gain of the amplifier 72 of the output circuit 71. However, by making the gain of the transistor M1 of each pixel PX variable, the gain may be adjusted at the step of outputting the voltage signal from each pixel PX. The pixel size of the pixel PX of the FPD 13 is larger than that of a small-size solid-state imaging apparatus used in a digital camera. Hence, a variable gain amplifier can be used in each pixel PX of the FPD 13.

In addition, in the description of the example in the above-mentioned embodiment, when the image synthesizing section 83 generates the synthesized X-ray image, the synthesized X-ray image is generated using all the read X-ray images. However, the synthesized X-ray image may be generated using some of the read X-ray images. For example, the gain $\gamma_1$, which is set first, may be excessively large or excessively small, and thus large overflow or underflow may occur in the first X-ray image. In this case, when the synthesized X-ray image is generated using the X-ray image, large overflow or underflow is reduced, and several rereading operations are necessary until the synthesized X-ray image appropriate for observation is obtained. Hence, inappropriate X-ray images such as the X-ray images in which large overflow or underflow occurs are excluded, and the synthesized X-ray image may be generated. Whether or not the read X-ray image is appropriate to be used in the generation of the synthesized X-ray image can be determined from, for example, any or combination of a shape of the histogram shown in FIG. 6, the maximum value or the minimum value of the effective range E, the width of the effective range E, and the like. When overflow or underflow occurs multiple times, for example, a part or the entirety of the shape of the histogram in FIG. 6 may be deformed. Further, when the shape of the histogram is deformed, it may not be able to identify the effective range E, and even if it is possible to identify the effective range E, the maximum value may be closer to the value of the distribution B than a predetermined threshold value, the minimum value may be closer to 0 than the predetermined threshold value, and the width of the effective range E may be greater/less than the predetermined threshold value.

In addition, in the description of the example in the above-mentioned embodiment, when the evaluation value calculation section 83 calculates the evaluation value, the pixel values of all the pixels of the synthesized X-ray image (the X-ray image which is captured first) is acquired. However, the acquired pixel values do not necessarily have to precisely acquire the pixel values of all the pixels. Specifically, the pixel values are entirely acquired from the entire region of the X-ray image to the extent that the above-mentioned histogram analysis can be performed. The extent that the above-mentioned histogram analysis can be performed is an extent that the resolution and the X-ray image finally used in observation are not extremely different. Such an image as can be subjected to the histogram analysis may be used in generation of the synthesized X-ray image. Consequently, the X-ray image, which is acquired by binning and reading several pixels or performing thinning-out reading, (or the synthesized X-ray image generated using the X-ray image) can be used in the calculation of the evaluation value.

The embodiments of the present invention have been hitherto described, but the present invention is not limited to the embodiments, and various modifications may be made without departing from the technical scope of the present invention.

For example, in the embodiments, the rear-irradiation-type electronic cassette 12 has been described as an example. However, the scintillator from the incidence side of the X-rays and the surface-incidence-type electronic cassette disposed in order of the FPD may be appropriately used. Further, in the description of the example in the above-mentioned first to fifth embodiments, the FPD 13 is a CMOS type, but an image sensor having another aspect may be used if the nondestructive reading is possible. Furthermore, the indirect-conversion-type FPD 13 using the scintillator 41 has been described as an example, but it may be possible to use a direct-conversion-type FPD that directly converts X-rays into electric charge through an X-ray conversion layer such as amorphous selenium without using the scintillator.

Further, in the description of the example, the synchronization control for the start and the ending of the irradiation of X-rays is performed through communication of the synchronization signal between the X-ray generator and the X-ray imaging apparatus. The X-ray generator is formed of the X-ray source and the radiation source controller, and the X-ray imaging apparatus is formed of the electronic cassette and the console. However, the X-ray imaging apparatus may be provided with an irradiation detection sensor so as to have a function of self-detecting the start and the ending of the irradiation of X-rays. In such a manner, it is not necessary to communicate the synchronization signal between the X-ray generator and the X-ray imaging apparatus. In this case, the pixel of the FPD may be used as the irradiation detection sensor.

Further, in the description of the example, the X-ray imaging apparatus includes the electronic cassette and the console. However, a function of controlling the electronic cassette among functions of the console may be implemented as an imaging controller separate from the console, and the X-ray imaging apparatus may include three devices of the electronic cassette, the imaging controller, and the console. Furthermore, the function of the imaging controller is built into the electronic cassette. Instead thereof or in addition thereto, the function of the image processing section 26 may be built into the electronic cassette. Moreover, in addition to the imaging controller, the electronic cassette, the imaging controller, and the console may be integrated. For example, the function of the console may be built into the electronic cassette.

Further, the X-ray imaging apparatus of the present invention is not limited to the form of the electronic cassette, and a stationary-type X-ray imaging apparatus in which the FPD is built into the imaging stage may be used.

Further, in the description of the example, the driving circuit 51 or the circuit element formed on the circuit board 41 is mounted as the IC chip 46 separately from the image sensor 42, the ASIC constituting the reading circuit formed of the CDS circuit 68 and the like is mounted as the IC chip 47 separately from the image sensor 42. However, those are may be formed on the substrate of the image sensor 42. That is, the various circuits and the like may be integrated with the pixels PX and the like on a single-crystal silicon substrate. As described above, when the various circuits such as the driving circuit 51 and the CDS circuit 68 are integrated with the pixels PX and the like on the same substrate, it is possible to remove the IC chip and the flexible cable, and it also becomes easy to perform assembly. Hence, it is possible to reduce the costs thereof.

The present invention is not limited to X-rays, and may be applied to an imaging system using different radiation such as γ-rays.

What is claimed is:
1. A radiographic imaging apparatus comprising:
a radiographic image detection section that receives radiation, which is emitted from a radiation source and transmitted through a subject, and detects a radiographic image of the subject, the radiographic image detection section having a plurality of pixels, in which signal electric charges corresponding to amounts of the radiation incident are accumulated, and being capable of nondestructively reading data, which indicate the radiographic image based on the amounts of the accumulated signal electric charges, from the pixels;
an amplification section capable of amplifying signals corresponding to the signal electric charges and capable of varying gain used for reading the radiographic image when the radiographic image is read from the radiographic image detection section;
a determination section that obtains an evaluation value for evaluating the radiographic image based on pixel values in a predetermined region of the radiographic image which is read by setting the gain of the amplification section to an initial value, and binning and reading several pixels or performing thinning-out read- ing, and determines whether or not performing a rereading of the radiographic image is necessary based on the evaluation value; and a gain calculation section that calculates a new gain of the amplification section used at the time of the rereading based on the evaluation value when the rereading is determined to be necessary from a result of the determination performed by the determination section, wherein the gain of the amplification section is changed to a value of the new gain which is calculated by the gain calculation section, and the radiographic image is reread using the changed gain.

2. The radiographic imaging apparatus according to claim 1, wherein the determination section determines whether or not performing the rereading is necessary, based on an appearance frequency distribution of pixel values in the radiographic image which is read by binning and reading several pixels or performing thinning-out reading.

3. The radiographic imaging apparatus according to claim 2, wherein the determination section determines whether or not performing the rereading is necessary, based on an effective range that indicates a distribution of pixel values of pixels indicating the subject depending on the appearance frequency distribution.

4. The radiographic imaging apparatus according to claim 3, wherein the determination section extracts pixels belonging to the effective range, sets an average value of pixel values of the extracted pixels as the evaluation value, and determines whether or not the rereading is necessary, by determining that the rereading is not necessary when the evaluation value is in the predetermined range and determining that the rereading is necessary when the evaluation value is outside of the predetermined range.

5. The radiographic imaging apparatus according to claim 3, wherein the determination section sets an average value between a maximum value and a minimum value of the effective range as the evaluation value, and determines whether or not performing the rereading is necessary.

6. The radiographic imaging apparatus according to claim 3, wherein the determination section sets an amount of deviation between a width of the effective range and a predetermined width as the evaluation value, and determines whether or not performing the rereading is necessary.

7. The radiographic imaging apparatus according to claim 1, further comprising an image synthesizing section that generates a single synthesized radiographic image by using a plurality of the radiographic images which is read by binning and reading several pixels or performing thinning-out reading and are obtained by changing and reading the gain of the amplification section through the first reading and the rereading.

8. The radiographic imaging apparatus according to claim 7, wherein the image synthesizing section generates the synthesized radiographic image by replacing a pixel, of which a pixel value is saturated, in the radiographic image which is read with a high gain, with a pixel corresponding to the read radiographic image which is read with a subsequent high gain, preferentially using pixels of the radiographic image which is read with the high gain.

9. The radiographic imaging apparatus according to claim 1, wherein the initial value of the gain of the amplification section is determined by imaging conditions that define a dosing amount of rays emitted by a radiation source.

10. The radiographic imaging apparatus according to claim 1, wherein the gain of the amplification section calculated by the gain calculation section is less than that at the time of the previous reading of the radiographic image.

11. A radiographic imaging system comprising:
a radiation source; and
a radiographic imaging apparatus according to claim 1, that receives radiation, which is emitted from the radiation source and transmitted through a subject, and radiographs a radiographic image of the subject.

12. A radiographic imaging method comprising:
a signal electric charge accumulation step of accumulating signal electric charges corresponding to amounts of radiation, which is emitted onto a subject and is incident into a plurality of pixels, through a radiographic image detection section having the plurality of pixels, which receives the radiation and detects a radiographic image, and being capable of nondestructively reading data, which indicate the radiographic image, from the pixels;
a radiographic image reading step of reading the radiographic image by amplifying signals corresponding to the signal electric charges through an amplification section which is capable of amplifying the signals and is capable of varying gain used for reading the radiographic image when the radiographic image is read from the radiographic image detection section;
a rereading necessity determination step of obtaining an evaluation value for evaluating the radiographic image based on pixel values in a predetermined region of the radiographic image which is read by setting the gain of the amplification section to an initial value, and binning and reading several pixels or performing thinning-out reading, and determining whether or not performing a rereading of the radiographic image is necessary based on the evaluation value;
a gain calculation step of calculating a new gain of the amplification section used at the time of the rereading based on the evaluation value when the rereading is determined to be necessary from a result of the determination as to whether or not performing the rereading is necessary; and
a rereading step of changing the gain of the amplification section to the calculated gain and rereading the radiographic image using the calculated gain.

13. A radiographic imaging apparatus comprising:
a radiographic image detection section that receives radiation, which is emitted from a radiation source and transmitted through a subject, and detects a radiographic image of the subject, the radiographic image detection section having a plurality of pixels, in which signal electric charges corresponding to amounts of the radiation incident are accumulated, and being capable of nondestructively reading data, which indicates the radiographic image based on the amounts of the accumulated signal electric charges, from the pixels;
an amplification section capable of amplifying signals corresponding to the signal electric charges and capable of varying gain used for reading the radiographic image when the radiographic image is read from the radiographic image detection section;
an image synthesizing section that outputs the radiographic image, which is read first by the radiographic image detection section, as a synthesized radiographic image when the radiographic image is read first by setting the gain of the amplification section to an initial value, and binning and reading several pixels or performing thinning-out reading, and synthesizes a plurality of the radiographic images, which are read from the radiographic image detection section through the rereading by binning and reading several pixels or performing thinning-out reading, so as to generate a synthesized radiographic image when the plurality of the radiographic images is read;

a determination section that obtains an evaluation value for evaluating the radiographic image based on pixel values in a predetermined region of the synthesized radiographic image, and determines whether or not performing a rereading of the radiographic image is necessary based on the evaluation value; and a gain calculation section that calculates a new gain of the amplification section used at the time of the rereading based on the evaluation value when the rereading is determined to be necessary from a result of the determination performed by the determination section, wherein the gain of the amplification section is changed to a value of the new gain which is calculated by the gain calculation section, the radiographic image is reread using the changed gain, and a new synthesized radiographic image including the new radiographic image, which is obtained through the rereading, is generated.

14. The radiographic imaging apparatus according to claim 13, wherein the image synthesizing section generates the new synthesized radiographic image including the new radiographic image when the new radiographic image is obtained through the rereading.

15. The radiographic imaging apparatus according to claim 13, wherein the image synthesizing section generates the synthesized radiographic image by averaging the plurality of the radiographic images.

16. The radiographic imaging apparatus according to claim 13, wherein the image synthesizing section generates the synthesized radiographic image by replacing a pixel, of which a pixel value is saturated, in the radiographic image which is read with a high gain, with a pixel corresponding to the read radiographic image which is read with a subsequent high gain, preferentially using pixels of the radiographic image which is read with the high gain.

17. The radiographic imaging apparatus according to claim 14, wherein the gain calculation section calculates a gain used at the time of subsequent rereading whenever the new synthesized radiographic image is generated through the rereading.

18. The radiographic imaging apparatus according to claim 13, wherein the initial value of the gain of the amplification section is set in advance, and is determined by imaging conditions that define a dosing amount of rays emitted by a radiation source.

19. The radiographic imaging apparatus according to claim 13, wherein the gain of the amplification section calculated by the gain calculation section is less than that at the time of the previous reading of the radiographic image.

20. The radiographic imaging apparatus according to claim 13, wherein the gain calculation section calculates the gain of the amplification section such that high and small gains are alternately repeated whenever the rereading is performed.

21. The radiographic imaging apparatus according to claim 13, wherein the determination section determines whether or not performing the rereading is necessary, based on an appearance frequency distribution of pixel values in the synthesized radiographic image.

22. The radiographic imaging apparatus according to claim 21, wherein the determination section determines whether or not performing the rereading is necessary, based on an effective range that indicates a distribution of pixel values of pixels indicating the subject depending on the appearance frequency distribution.

23. The radiographic imaging apparatus according to claim 22, wherein the determination section extracts pixels belonging to the effective range, sets an average value of pixel values of the extracted pixels as the evaluation value, and determines whether or not the rereading is necessary, by determining that the rereading is not necessary when the evaluation value is in the predetermined range and determining that the rereading is necessary when the evaluation value is outside of the predetermined range.

24. The radiographic imaging apparatus according to claim 22, wherein the determination section sets an average value between a maximum value and a minimum value of the effective range as the evaluation value, and determines whether or not performing the rereading is necessary.

25. The radiographic imaging apparatus according to claim 22, wherein the determination section sets an amount of deviation between a width of the effective range and a predetermined width as the evaluation value, and determines whether or not performing the rereading is necessary.

26. The radiographic imaging apparatus according to claim 13, wherein when determining that the rereading is necessary, the determination section further evaluates an amount of noise of the synthesized radiographic image, and determines the number of times the rereading is performed.

27. The radiographic imaging apparatus according to claim 26, wherein the determination section evaluates graininess of the synthesized radiographic image as the amount of noise.

28. The radiographic imaging apparatus according to claim 26, wherein the determination section evaluates the amount of noise based on the synthesized radiographic image generated from the radiographic image, which is read first, and the radiographic image which is read second.

29. A radiographic imaging system comprising:
a radiation source; and
a radiographic imaging apparatus according to claim 13, that receives radiation, which is emitted from the radiation source and transmitted through a subject, and radiographs a radiographic image of the subject.

30. A radiographic imaging method comprising:
a signal electric charge accumulation step of accumulating signal electric charges corresponding to amounts of radiation, which is emitted onto a subject and is incident into a plurality of pixels, through a radiographic image detection section having the plurality of pixels, which receives the radiation and detects a radiographic image, and being capable of nondestructively reading data, which indicates the radiographic image, from the pixels;
a radiographic image reading step of reading the radiographic image by amplifying signals corresponding to the signal electric charges through an amplification section which is capable of amplifying the signals and is capable of varying gain used for reading the radiographic image when the radiographic image is read from the radiographic image detection section;
an image synthesis step of outputting the radiographic image, which is read first by the radiographic image detection section, as a synthesized radiographic image when the radiographic image is read first by setting the gain of the amplification section to an initial value, and binning and reading several pixels or performing thinning-out reading, and synthesizing a plurality of the radiographic images, which are read from the radiographic image detection section through the rereading by binning and reading several pixels or performing thinning-out reading, so as to generate a synthesized radiographic image when the plurality of the radiographic images is read;

a rereading necessity determination step of obtaining an evaluation value for evaluating the radiographic image based on pixel values in a predetermined region of the radiographic image, and determining whether or not performing a rereading of the radiographic image is necessary based on the evaluation value;

a gain calculation step of calculating a new gain of the amplification section used at the time of the rereading based on the evaluation value when it is determined that the rereading is necessary from a result of the determination as to whether or not it is necessary to perform the rereading;

a rereading step of changing the gain of the amplification section to the calculated gain and rereading the radiographic image using the changed gain; and a second image synthesis step of generating a new synthesized radiographic image including the new radiographic image which is obtained through the rereading.

* * * * *